United States Patent
Ito et al.

(10) Patent No.: US 8,303,489 B2
(45) Date of Patent: Nov. 6, 2012

(54) ENDOSCOPE WITH BUILT-IN FILTERING MEANS

(75) Inventors: Jin Ito, Tokyo (JP); Tsutomu Okada, Tachikawa (JP); Yasuhito Kura, Hachioji (JP)

(73) Assignee: Olympus Medical Systems Corp., Tokyo (JP)

( * ) Notice: Subject to any disclaimer, the term of this patent is extended or adjusted under 35 U.S.C. 154(b) by 1137 days.

(21) Appl. No.: 11/582,170

(22) Filed: Oct. 17, 2006

(65) Prior Publication Data

US 2007/0088199 A1    Apr. 19, 2007

(30) Foreign Application Priority Data

Oct. 17, 2005 (JP) ................................. 2005-302182
Oct. 17, 2005 (JP) ................................. 2005-302184
Oct. 17, 2005 (JP) ................................. 2005-302186

(51) Int. Cl.
*A61B 1/00* (2006.01)
*A61B 10/00* (2006.01)
*A61M 1/00* (2006.01)

(52) U.S. Cl. ........ 600/159; 600/154; 600/158; 600/565; 604/319

(58) Field of Classification Search .................. 600/154, 600/153, 563, 565, 571, 104, 156–159, 562, 600/573; 606/180, 113–115; 604/317, 319–326
See application file for complete search history.

(56) References Cited

U.S. PATENT DOCUMENTS

| | | | | |
|---|---|---|---|---|
| 4,957,492 A | * | 9/1990 | McVay | 604/319 |
| 5,035,688 A | * | 7/1991 | Inui | 604/190 |
| 5,363,860 A | * | 11/1994 | Nakao et al. | 600/573 |
| 5,456,689 A | * | 10/1995 | Kresch et al. | 606/180 |
| 5,483,951 A | | 1/1996 | Frassica et al. | |
| 5,971,917 A | * | 10/1999 | Komi et al. | 600/159 |
| 6,013,048 A | | 1/2000 | Podany et al. | |
| 6,110,127 A | | 8/2000 | Suzuki | |

(Continued)

FOREIGN PATENT DOCUMENTS

DE    199 05 311 A1    8/1999

(Continued)

OTHER PUBLICATIONS

Translation of JP62074804.*

*Primary Examiner* — Matthew J Kasztejna
*Assistant Examiner* — Ryan Henderson
(74) *Attorney, Agent, or Firm* — Scully, Scott, Murphy & Presser, PC

(57) ABSTRACT

The rear end side of treatment equipment-side duct which enables treatment equipment provided within an insertion unit to be inserted, and which also serves as a suction duct, is disposed generally in parallel with the tip side of a suction-side duct extending forward from a universal cable side so as to be an opening end, and both opening ends are detachably attached with a filter unit in which a forceps plug portion serving as a suction duct opening, and a filter portion for retrieving (storing) tissue by suction are provided, and a suction switchover valve for performing a suction switchover operation is provided at the backward side thereof, thereby enabling retrieval of tissue without influence of the periphery of the suction switchover valve. Thus, defects due to a long duct can be eliminated, and tissue can be retrieved without influence of the periphery of the suction switchover valve.

10 Claims, 13 Drawing Sheets

U.S. PATENT DOCUMENTS

| | | | | |
|---|---|---|---|---|
| 6,142,956 A * | 11/2000 | Kortenbach et al. | | 600/564 |
| 6,331,165 B1 * | 12/2001 | Turturro et al. | | 600/562 |
| 6,428,316 B1 * | 8/2002 | Rodriquez | | 433/92 |
| 7,244,236 B2 * | 7/2007 | Merkle | | 600/575 |
| 8,070,756 B2 * | 12/2011 | Secrest et al. | | 606/113 |
| 8,088,079 B2 * | 1/2012 | Kaye et al. | | 600/562 |
| 2004/0220452 A1 * | 11/2004 | Shalman | | 600/157 |
| 2005/0027165 A1 * | 2/2005 | Rovegno | | 600/154 |

FOREIGN PATENT DOCUMENTS

| | | |
|---|---|---|
| JP | 62-74804 | 5/1987 |
| JP | 06-054853 | 3/1994 |
| JP | 07184847 A * | 7/1995 |
| JP | 11-267089 A | 10/1999 |
| JP | 2000-237126 A | 9/2000 |
| JP | 2005-211453 A | 8/2005 |
| WO | WO 99/20096 | 4/1999 |

* cited by examiner

ENDOSCOPE WITH BUILT-IN FILTERING MEANS

CROSS REFERENCES TO RELATED APPLICATIONS

This application claims benefit of Japanese Application Nos. 2005-302182, 2005-302184 and 2005-302186 filed on Oct. 17, 2005 the contents of which are incorporated by this reference.

BACKGROUND OF THE INVENTION

1. Field of the Invention

The present invention relates to an endoscope for performing endoscopy by inserting an insertion unit into a body cavity or the like.

2. Description of the Related Art

In recent years, endoscopes have been widely employed in the medical-application field and so forth. These endoscopes can optically observe a portion to be checked by inserting an insertion unit.

In the medical-application field, endoscopes are employed for endoscopy for inserting an insertion unit into a body cavity, and optically observing a portion to be checked such as an affected portion or the like using an illumination optical system and an observation optical system provided in the tip portion of the insertion unit.

Also, in endoscopy, biopsy is sometimes performed by inserting treatment equipment within a channel duct, excising of tissue of a portion to be checked, and retrieving the excised tissue from the body as necessary.

In the event of retrieving the excised tissue from the body, a surgeon who is a doctor sometimes employs a method for removing an endoscope insertion unit from the body along with treatment equipment. However, an operation for removing and reinserting the insertion unit sometimes takes time and effort.

Accordingly, for example, the conventional example in Japanese Unexamined Patent Application Publication No. 6-54853 has disclosed an arrangement wherein a tissue-retrieving filter is disposed between a suction connector at the side toward the operator of the endoscope and a suction pump connected with this suction connector, and the tissue which has passed through a duct by suction using the suction pump is retrieved by the filter.

SUMMARY OF THE INVENTION

An endoscope according to the present invention comprises a suction duct having one end to which a suction source is connected, a suction switchover unit provided on the suction duct, and a tissue-retrieving unit disposed on an opposite side of the one end of the suction duct to which the suction source is connected, with respect to a position of the suction switchover unit.

As in the above arrangement, providing the tissue-retrieving filter portion further toward the tip side of the insertion unit of the endoscope than the suction switchover valve enables a defect due to a long duct to be eliminated, and also realizes an endoscope suitable for retrieving tissue without receiving influence of the periphery of the suction switchover valve.

According to the present invention thus described, retrieving of tissue can be performed without passing tissue through a long duct, and also without receiving influence of the periphery of the suction switchover valve.

The above and other objects, features and advantages of the invention will become more clearly understood from the following description referring to the accompanying drawings.

DETAILED DESCRIPTION OF THE PREFERRED EMBODIMENTS

Hereinafter, embodiments of the present invention will be described with reference to the drawings.

(First Embodiment)

A first embodiment of the present invention will be described with reference to FIGS. 1 through 7.

Figure 1:
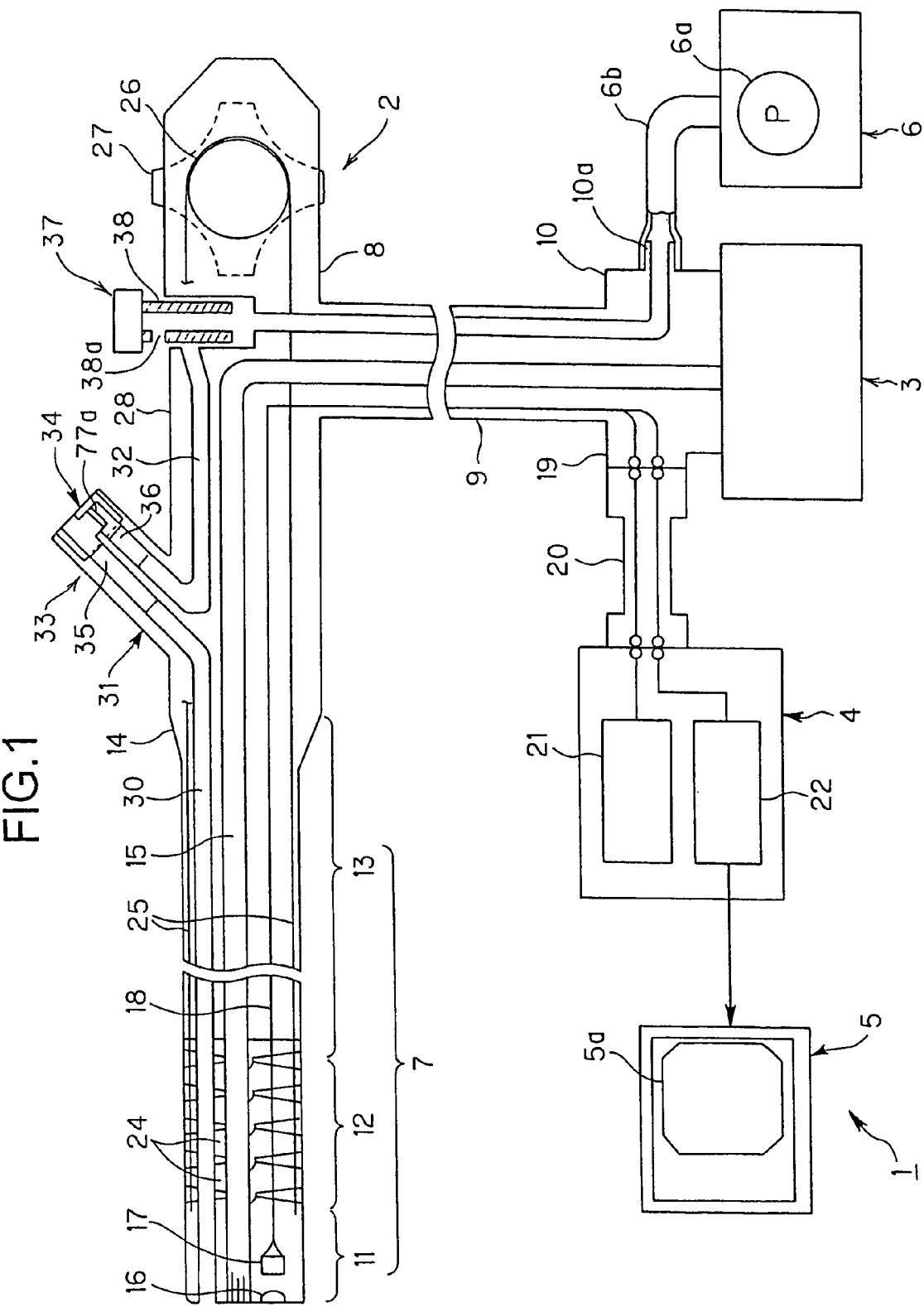
FIG. 1 is an overall configuration diagram of an endoscope system including an endoscope according to a first embodiment of the present invention.

As illustrated in FIG. 1, an endoscope 1 comprises an electronic endoscope (hereinafter, abbreviated simply as "endoscope") 2 according to the first embodiment, a light source device 3 for supplying illumination light to the endoscope 2, a signal processing device 4 for subjecting the image capturing signal to be output from the endoscope 2 to signal processing, a color monitor 5 for displaying the picture signal to be output from the signal processing device 4 on a screen, and a suction device 6 which has built in a suction pump 6a, as a suction source, for performing a suction operation.

The endoscope 2 comprises a slender endoscope insertion unit (hereinafter, simply referred to as an insertion unit) 7, a thick-width operating unit 8 serially connected to the rear end side of the insertion unit 7, and a universal cable 9 extending from the side portion of the operating unit 8. The end portion of the universal cable 9 is provided with a connector 10, and the connector 10 is detachably connected to the light source device 3.

Also, the connector 10 is provided with a suction connector (suction collet) 10a serving as an end portion at the side toward the operator of a later-described suction-side duct 32 inserted into the universal cable 9. The suction connector 10a is connected to the suction device 6 via a suction tube 6b.

The insertion unit 7 includes a hard tip portion 11, a flexible bending portion 12 which is formed on the rear end of the tip portion 11, and a long flexible portion 13 having flexibility which is formed on the rear end of the bending portion. The rear end of the flexible portion 13 is connected to the front end of the operating unit 8. The rear end outer circumference of the flexible portion 13 is provided with a folding-prevention portion 14 in a tapered shape.

A light guide 15 having flexibility and including a fiber bundle which has a function for transmitting illumination light is inserted into the insertion unit 7, operating unit 8, and universal cable 9. Upon a light guide connector protruding from the connector 10 being connected to the light source device 3, the light guide 15 guides and transmits the illumination light from an unshown lamp within the light source device 3 up to the end face of the light guide connector.

The illumination light transmitted by the light guide 15 is emitted forward from the tip face fixed to the illumination window of the tip portion 11, and illuminates a subject such as an affected portion or the like. An objective lens 16 attached to an observation window provided in the tip portion 11 adjacent to the illumination window forms an optical image of the illuminated subject at image-forming position thereof. At the image-forming position is a charge-coupled device (abbreviated as CCD) 17 serving as an image capturing device including a photoelectric conversion function disposed, which converts the optical image into electric signals. Note that the charge-coupling device may be a CMOS.

The CCD 17 is connected to one end of a signal cable 18. The signal cable 18 is inserted through the insertion unit 7, and rear end thereof is connected to the electric connector 19 of the connector 10. The electric connector 19 is connected to the signal processing device 4 via an external cable 20.

A drive circuit 21 is provided within the signal processing device 4. The CCD drive signal to be output from the drive circuit 21 is applied to the CCD 17. Upon the CCD drive signal being applied, the CCD 17 outputs the image capturing signal which is subjected to photoelectric conversion. The image capturing signal is input to a signal processing circuit 22 within the signal processing device 4. Subsequently, the image capturing signal is subjected to signal processing by the signal processing circuit 22 to be converted into a standard picture signal. The standard picture signal is input to the color monitor 5, and the endoscope image captured by the CCD 17 is color-displayed on an endoscope image display region 5a.

The bending portion 12 provided adjacent to the tip portion 11 is configured by a large number of ring-shaped bending pieces 24 being mutually connected with adjacent bending pieces 24 at vertically or horizontally corresponding positions by rivets or the like so as to move rotationally. The rear end of a bending wire 25 fixed to the bending piece 24 at the leading edge or the tip portion 11 is connected to a sprocket 26 within the operating unit 8, and the shaft of the sprocket 26 is attached with a bending operating knob 27 for performing a bending operation (FIG. 1 illustrates the outline of a bending mechanism in the vertical or horizontal direction alone for the sake of facilitating description).

An arrangement is made wherein one of a pair of the bending wire 25 disposed in the vertical direction or in the horizontal direction is subjected to traction, and the other is subjected to relaxation, and the bending portion 12 can be bent at the bending wire 25 side subjected to traction by performing an operation for moving the bending operating knob 27 rotationally.

The operating unit 8 is provided with a gripper 28 further forward than a position where the bending operating knob 27 is provided. An arrangement is made wherein a surgeon can perform operation of the bending operating knob 27, or the like with one hand (a finger such as the thumb or the like which is not used for gripping the gripper 28) gripping the gripper 28.

Also, the rear end side of treatment equipment-side duct 30 provided within the insertion unit 7 is disposed generally in parallel with the tip side of a suction-side duct 32 extending toward the forward side from the universal cable 9 side via the operating unit 8 in treatment equipment insertion portion 31 provided around the front end of the gripper 28, and a duct separating portion 33 in which both opening ends are separated (segmentized) is formed.

The treatment equipment insertion portion 31 forming the duct separating portion 33 has detachably mounted thereupon a filter unit 34 constituting a tissue-retrieving unit including a forceps-plug function which enables treatment equipment to be inserted, and also retains the duct in an obstructive state when treatment equipment is not inserted, and a filter function of retrieving tissue.

Thus, with the endoscope 2 according to the present embodiment, the treatment equipment-side duct 30 for inserting treatment equipment is formed within the insertion unit 7. Also, in the inside of the treatment equipment insertion portion 31 provided around the rear end of the insertion unit 7, the treatment equipment-side duct 30 is extended to an oblique backward side, and the rear end thereof is opened as the (treatment equipment-side collet) opening portion 35a of the treatment equipment-side collet 35. In the inside of the endoscope 2, the treatment equipment-side duct 30 includes no branch portion, thereby configured so as to improve ease of insertion of treatment equipment, and the cleaning properties by insertion of a brush.

The opening portion 35a of the treatment equipment-side collet 35 (see FIG. 2, FIG. 5, and the like) is provided with treatment equipment plug (abbreviated as forceps plug portion) 41 in the filter unit 34 (see FIG. 4, FIG. 5, and the like), and treatment equipment is inserted from the rear end side of the forceps plug portion 41.

Also, to the duct separating portion 33, the tip side portion of the suction-side duct 32 extending from the operating unit 8 side is disposed generally in parallel with the rear end side of the treatment equipment-side duct 30. The duct separating portion 33 is adjacent to the treatment equipment-side collet 35, and the (suction-side collet) opening portion 36a of the suction-side collet 36 at the tip of the duct separating portion 33 (see FIG. 3, FIG. 5, and so forth) is opened.

Figure 3:
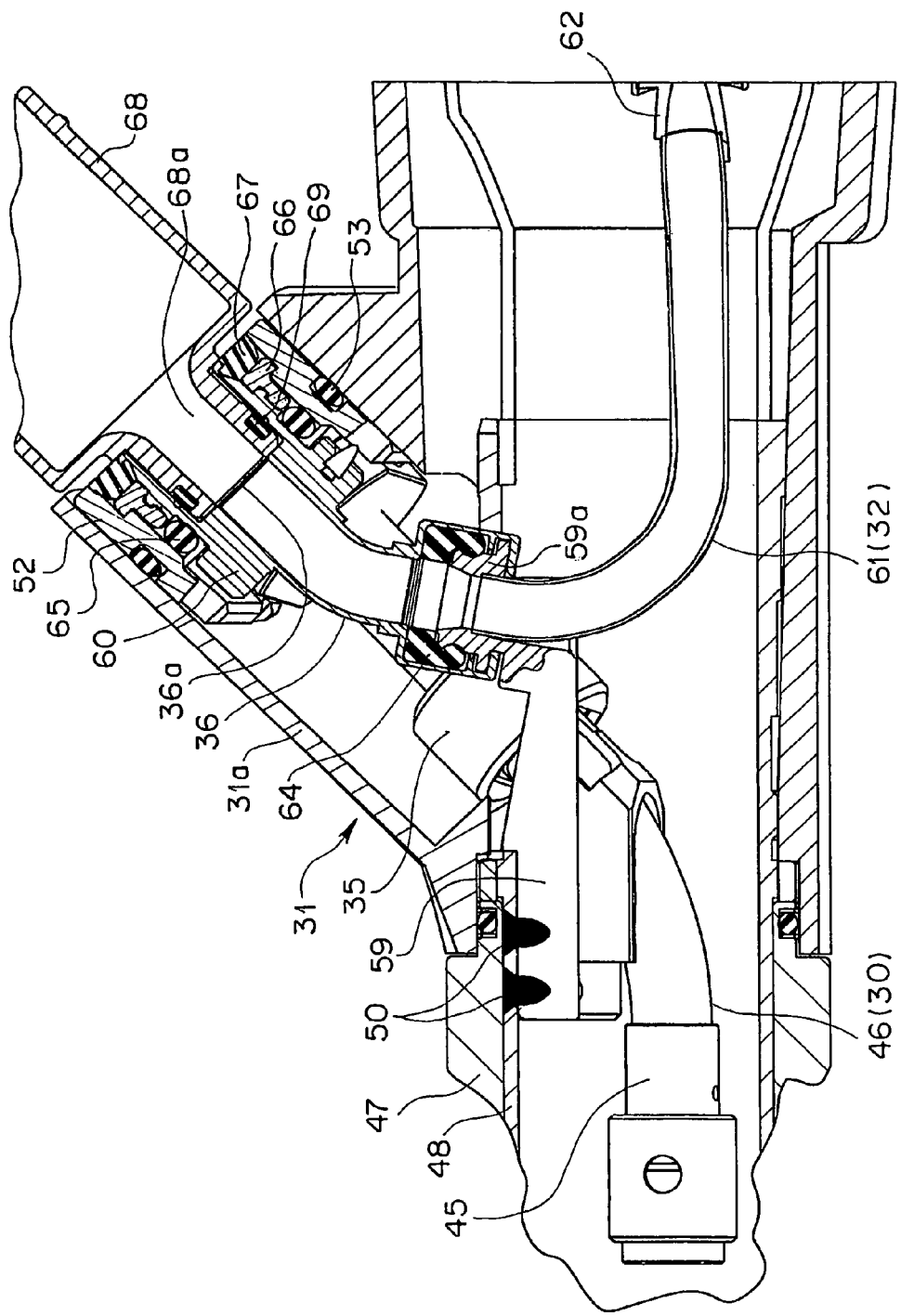
FIG. 3 is a cross-sectional view illustrating the internal configuration along a suction-side collet in the treatment equipment insertion portion according to the first embodiment.
Figure 5:
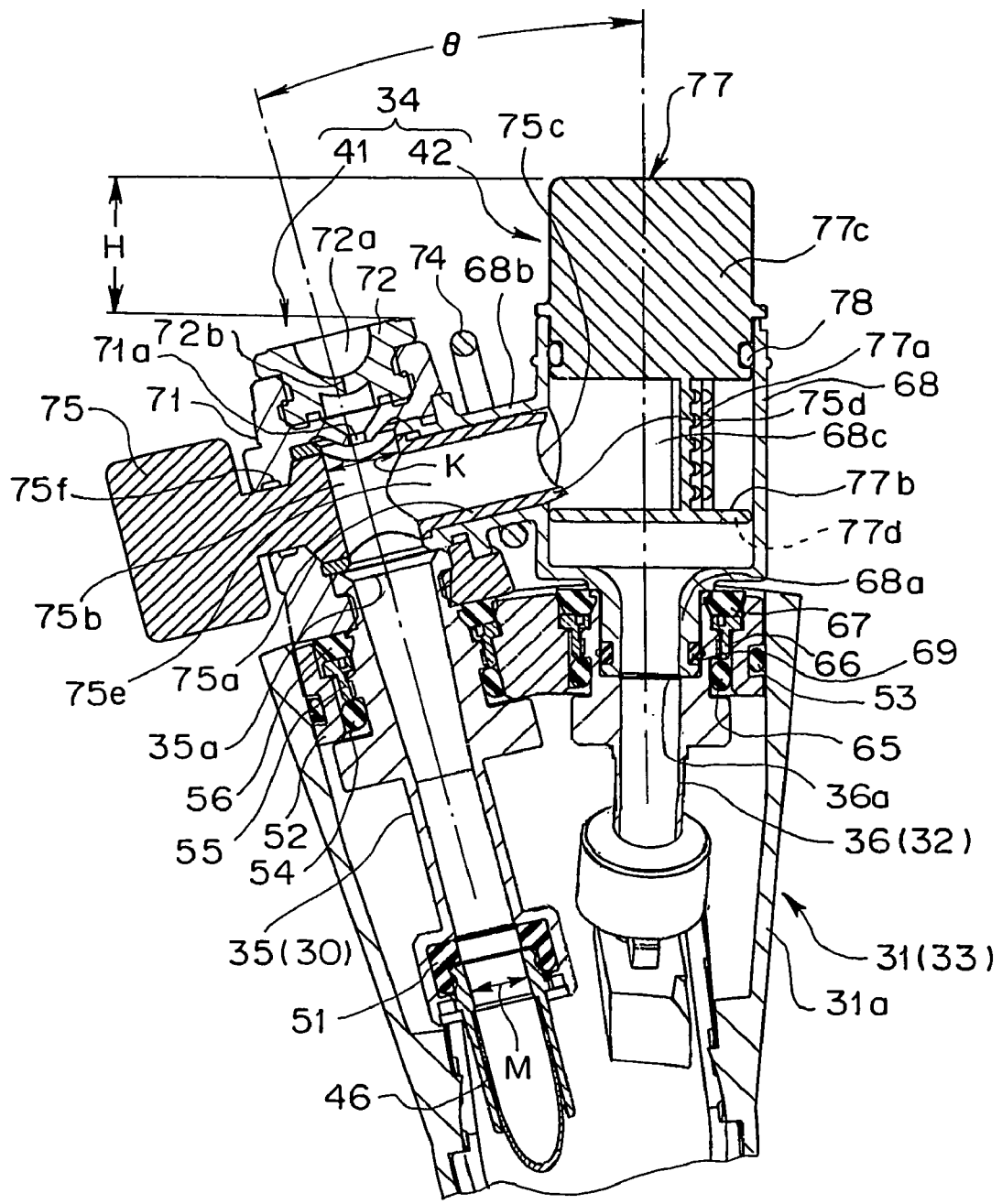
FIG. 5 is a cross-sectional view illustrating the configuration of the periphery of the treatment equipment-side collet and the suction-side collet taken along the V-V cross-section in FIG. 2.

To the opening portion 36a of the suction-side collet 36, a filter portion 42 for retrieving tissue serving as the tissue-retrieving portion in the filter unit 34, and also serving as tissue-retrieving means is mounted (see FIG. 3, FIG. 5, and so forth).

Figure 6:
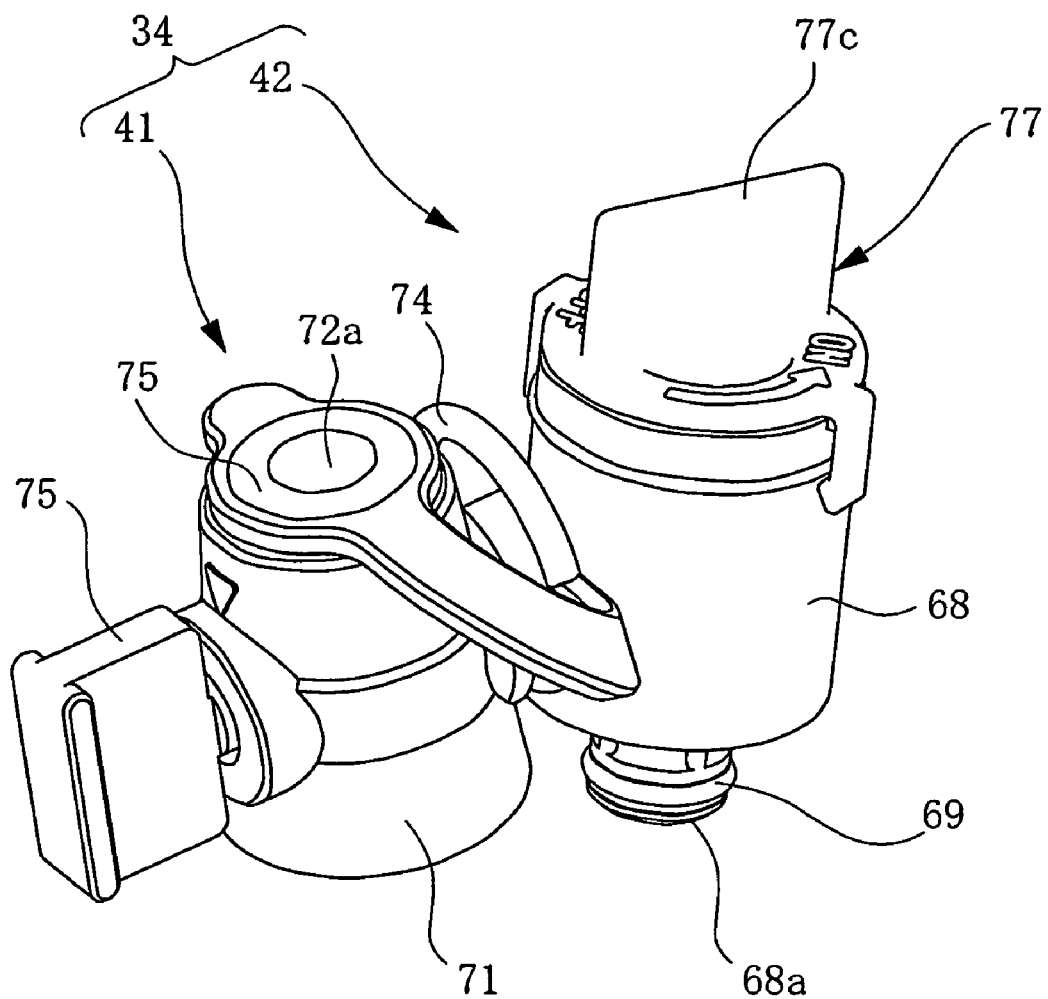
FIG. 6 is a perspective view illustrating the filter unit in an assembled state with the endoscope according to the first embodiment.

Note that FIG. 1 illustrates the outline of the duct separating portion 33 and the filter unit 34, and in FIG. 1, the treatment equipment-side collet 35 and the suction-side collet 36 are adjacently illustrated within the page, but actually, they are formed adjacently in the direction perpendicular to the page in FIG. 1 (see FIGS. 5 and 6).

Also, the side face of the operating unit 8 is provided with a suction switchover valve 37, which is disposed on the way of the suction-side duct 32 inserted through the operating unit 8, serving as a suction switchover unit and suction switchover means for switching a non-suction state (abbreviated as suction-OFF) and a suction state (abbreviated as suction-ON).

The suction switchover valve 37 is formed by an inner cylinder 38 being slidably disposed within a cylindrical body provided on the side face of the operating unit 8. The opening of the bottom face in this cylindrical body is connected with the tip portion of the suction-side duct 32 extending from the universal cable 9 side connected to the suction device 6. Also, the opening of the side face of the cylindrical body is connected with the rear end of the suction-side duct 32 extending backward from the treatment equipment insertion portion 31 side.

Also, the inner side portion of the inner cylinder 38 is connected to the suction-side duct 32 extending from the universal cable 9 side. In the event that the suction switchover valve 37 is not operated, i.e., in a suction-OFF state, the inner cylinder 38 is connected to the outside by the opening portion 38a provided on the side portion of the upper end side.

Accordingly, in the event that the suction switchover valve 37 is in a suction-OFF state, the suction pump 6a which is set to a suction running state captures the air from the opening portion 38a, so does not perform a suction operation through the suction-side duct 32 further toward the tip side than the suction switchover valve 37.

The opening portion 38a is switched from a state connected to the outside to a state connected to the rear end of the suction-side duct 32 extending from the treatment equipment insertion portion 31 side by a surgeon performing an operation for pressing the suction switchover valve 37 against the elastic force of an unshown spring to push it into the bottom portion side of the cylindrical body.

In this state, the suction switchover valve 37 enters a state for performing a suction operation through the suction-side duct 32 further toward the tip side than the suction switchover valve 37 by the suction pump 6a which is set to a suction state. Thus, the suction-ON/OFF state is arranged so as to be switched by operating the suction switchover valve 37.

Next, description will be made in detail regarding the configuration of the periphery of the treatment equipment insertion portion 31, and the configuration of the filter unit 34 to be detachably mounted on this opening end with reference to FIGS. 2 through 7 according to the present embodiment.

Figure 2:
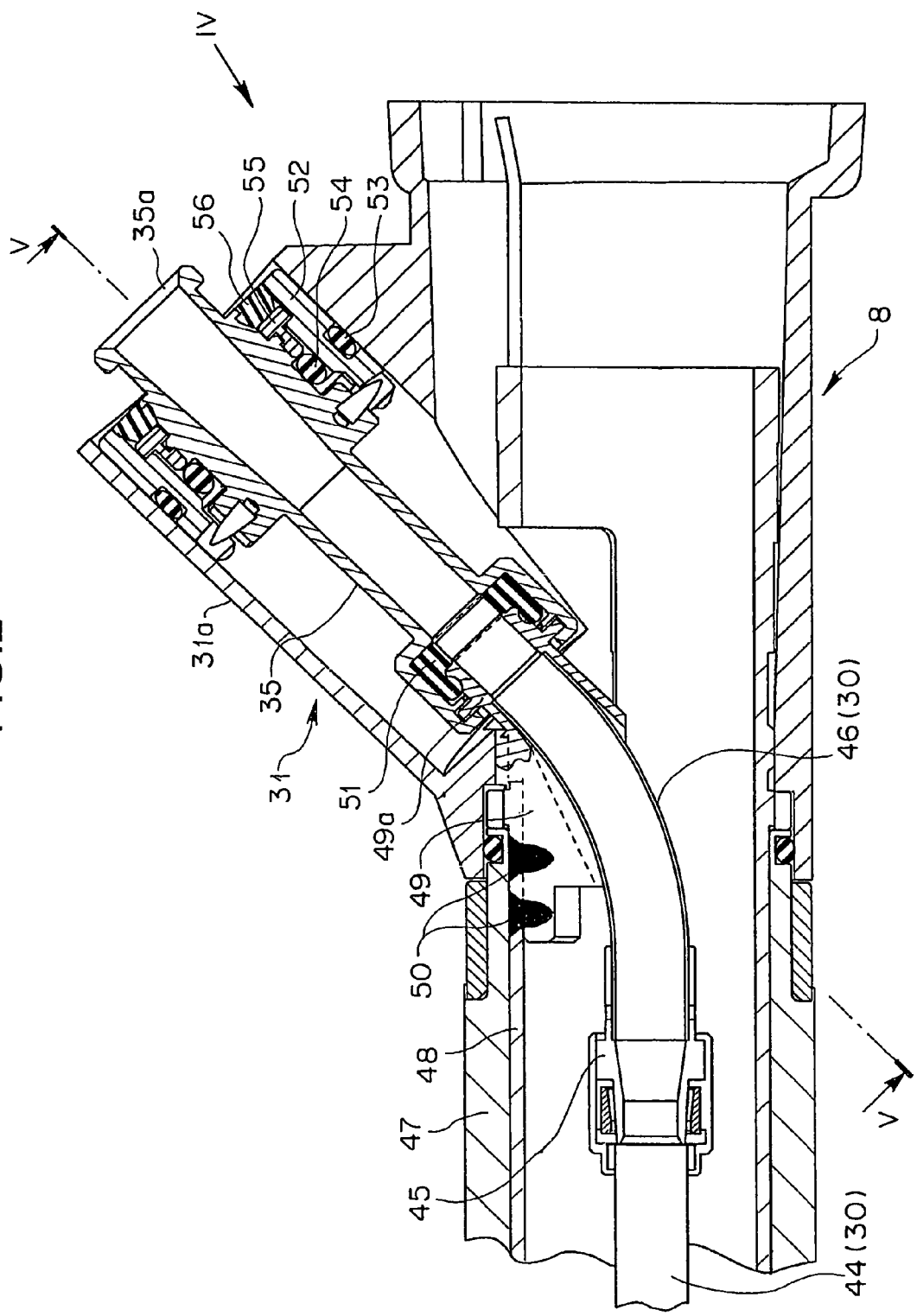
FIG. 2 is a cross-sectional view illustrating the internal configuration along treatment equipment-side collet in treatment equipment insertion portion in the endoscope according to the first embodiment.
Figure 4:
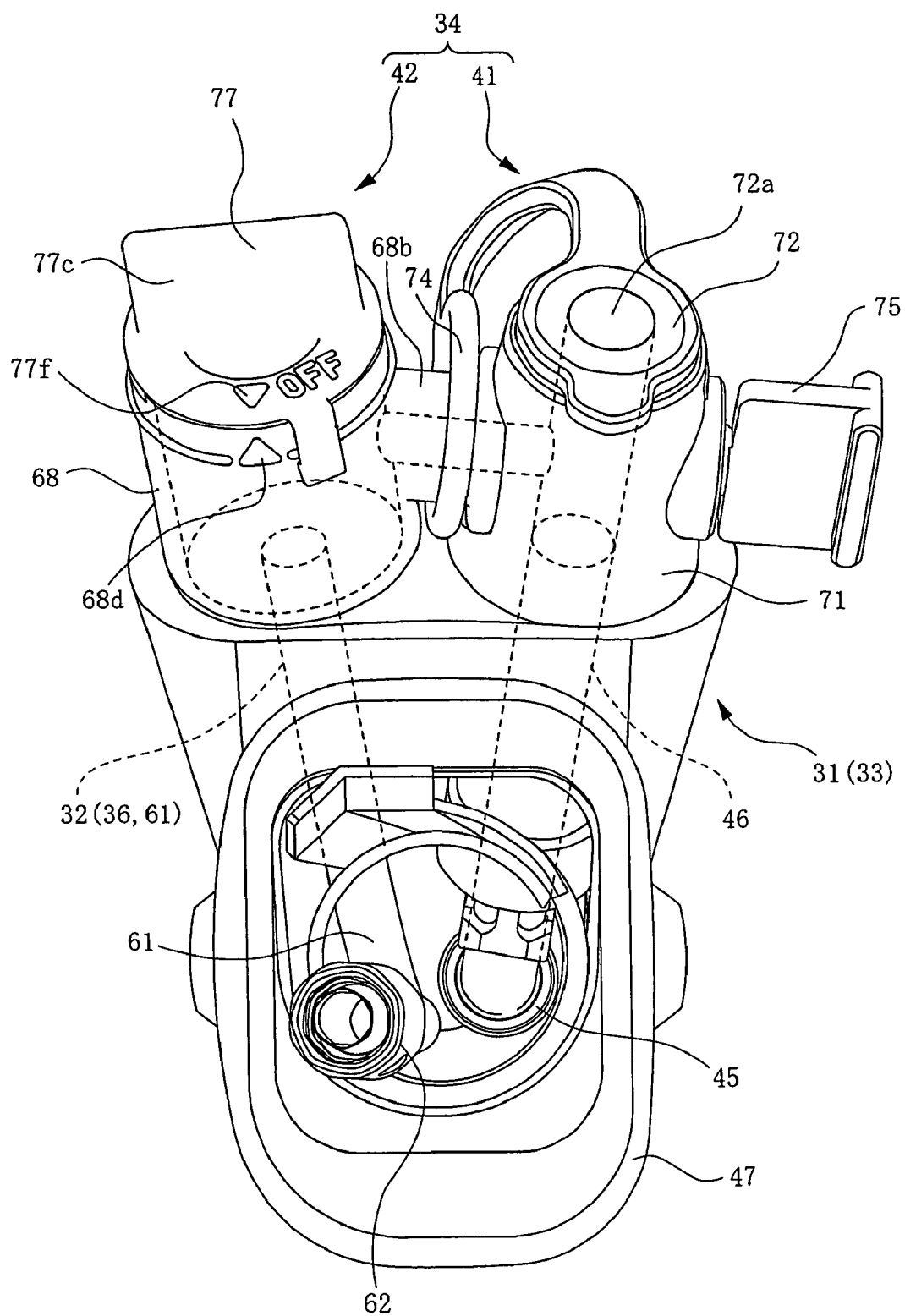
FIG. 4 is a diagram illustrating the periphery of a filter unit as viewed from the IV arrow visual direction in FIG. 2.
Figure 7:
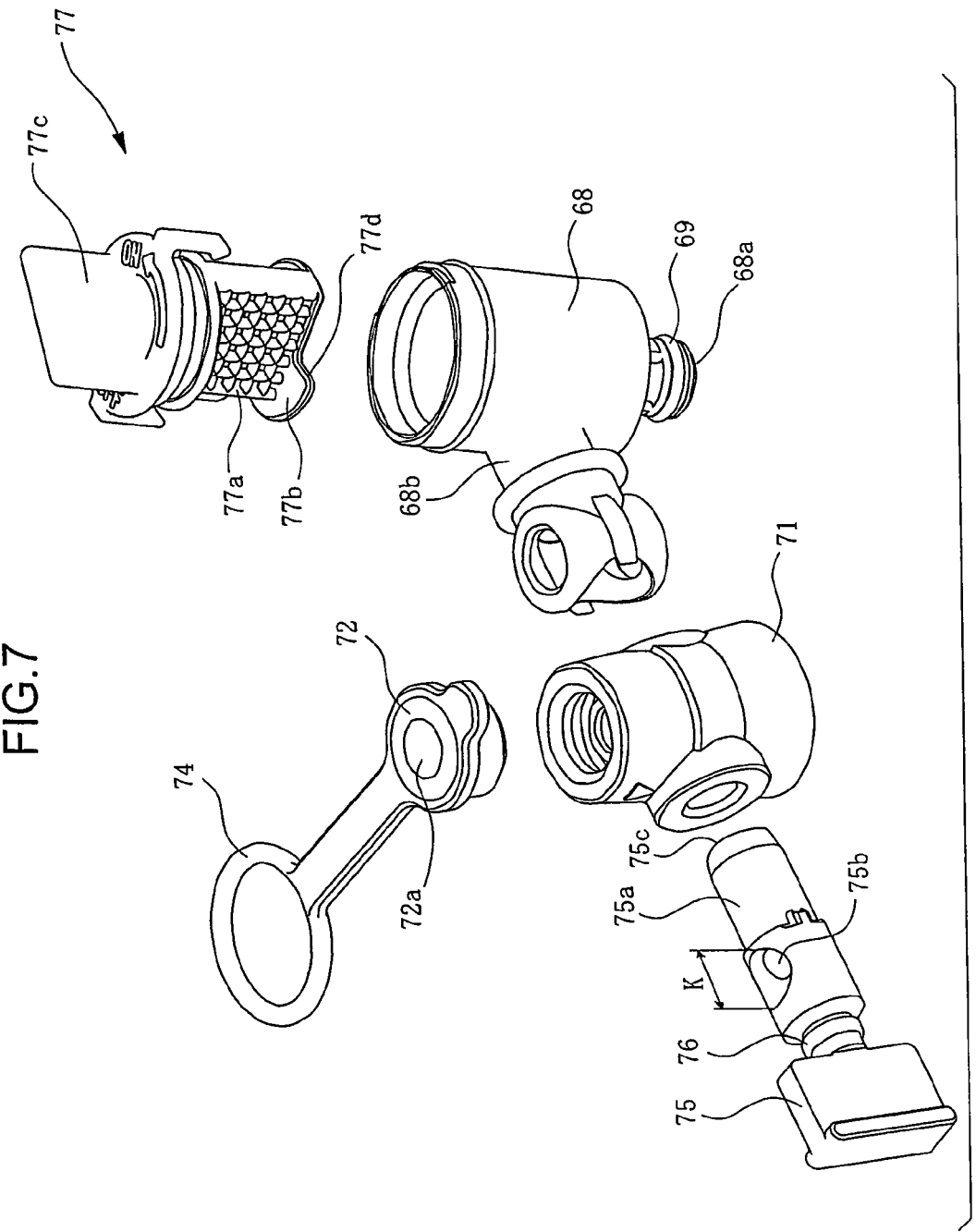
FIG. 7 is a perspective view illustrating the filter unit in a disassembled state with the endoscope according to the first embodiment.
Figure 8:
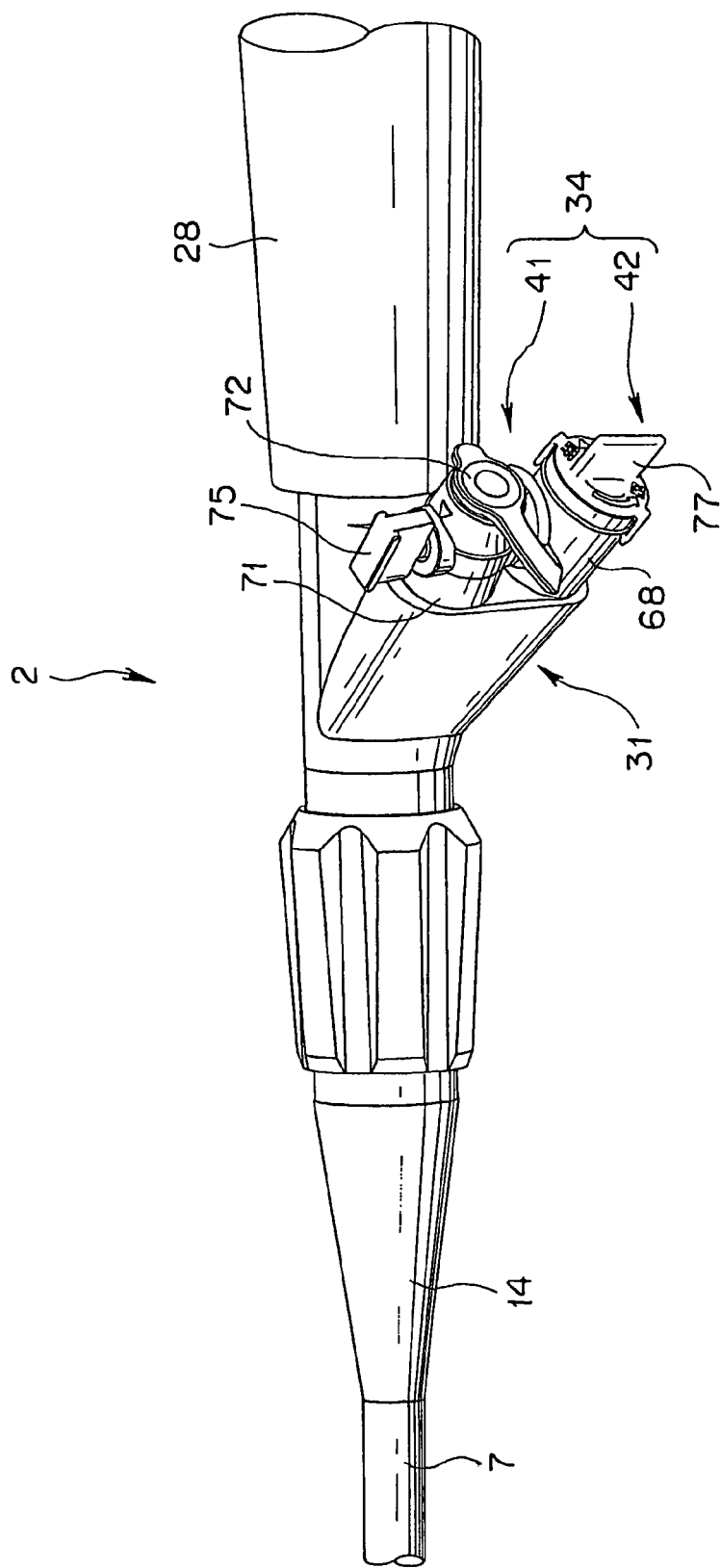
FIG. 8 is a perspective view illustrating the vicinity of the treatment equipment insertion portion with the endoscope according to the first embodiment.

FIG. 2 illustrates the internal configuration using a vertical cross-section along the treatment equipment-side collet 35 in the treatment equipment insertion portion 31, FIG. 3 illustrates the internal configuration using a vertical cross-section along the suction-side collet 36 in the treatment equipment insertion portion 31, FIG. 4 illustrates a part of the periphery of the filter unit 34 as viewed from the IV arrow visual direction in FIG. 2 as a cross-section, FIG. 5 illustrates the cross-sectional configuration of the periphery of the treatment equipment-side collet 35 and the suction-side collet 36 taken along the V-V cross-section in FIG. 2, FIG. 6 illustrates the filter unit 34 in an assembled state, FIG. 7 illustrates the filter unit 34 in a disassembled state, and FIG. 8 illustrates the vicinity of the treatment equipment insertion portion 31 in the endoscope.

Note that FIG. 4 illustrates the cross-section in a state in which retrieving of tissue is set so as not to be performed, and FIG. 5 illustrates the cross-section in a state in which retrieving of tissue is set so as to be performed.

The rear end of treatment equipment insertion tube 44 is extended to the inside of the gripper 28 from the insertion unit 7 side as illustrated in FIG. 2, and forms the treatment equipment-side duct 30 having a function for a duct (channel) into which treatment equipment is inserted, and a function for a suction duct through which tissue and the like are passed. The rear end of the treatment equipment insertion tube 44 is connected to the tip of treatment equipment-side pipe 46, which is bent via a connection collet 45, in a watertight and airtight manner.

The rear end side of the treatment equipment-side pipe 46 is fixed in the vicinity of an opening portion provided on the top face of a frame 48 provided within an exterior member 47 of the operating unit 8 by a fixing member 49. The tip portion of the fixing member 49 is fixed to the frame 48 by a screw 50, and the rear end of the treatment equipment-side pipe 46 is fitted into the cylinder portion 49a formed at the rear end side of the fixing member 49, and is fixed.

Also, the cylinder portion 49a fixed with the rear end of the treatment equipment-side pipe 46 is connected with the tip of the treatment equipment-side collet 35 disposed in a straight-pipe shape within the exterior member 31a of the treatment equipment insertion portion 31 via a packing 51 made of rubber in a watertight and airtight manner.

The treatment equipment-side collet 35 is disposed toward the oblique backward side from the axial direction of the insertion unit 7. The recessed portion of the rear end outer circumference of the treatment equipment-side collet 35 is disposed with a watertight and airtight O ring 54, and is fixed to the exterior member 31a via a fixing resin member 52 disposed between the exterior member 31a and the O ring 54.

The resin member 52 is fitted into the inner face of the exterior member 31a, and the recessed portions of the outer circumference and the inner circumference of the resin member 52 are disposed with a watertight and airtight O ring 53. The O ring 53 is fixed in an airtight manner by a nut 55 to be screwed into a male screw portion of the rear end outer circumferential face of the treatment equipment-side collet 35. Note that the upper end face of the nut 55 is covered with a rubber cover 56.

The rear end portion of the treatment equipment-side collet 35 somewhat protrudes from the end face protruding toward the oblique backward side of the exterior member 31a of the treatment equipment insertion portion 31, and opens at the treatment equipment-side collet opening portion 35a of rear end thereof. That is, the treatment equipment-side collet opening portion 35a constitutes the suction duct opening from which the treatment equipment is inserted.

In the upward direction perpendicular to the page in the treatment equipment-side collet 35 illustrated in FIG. 2, the tip side of the suction-side duct 32 is provided within the treatment equipment insertion portion 31 adjacent to the treatment equipment-side collet 35 as illustrated in FIGS. 3 and 5.

The suction-side duct tube making up the suction-side duct 32 of the operating unit 8 side is connected to the rear end of the bent suction-side pipe 61 via a connecting collet 62 in a watertight and airtight manner.

The bent suction-side pipe 61 is also fixed by the tip of the suction-side pipe 61 being fitted into the cylinder portion 59a formed at the rear end side of the fixing member 59.

Also, the cylinder portion 59a fixed with the tip of the suction-side pipe 61 is connected with the rear end of the suction-side collet 36 disposed within the exterior member 31a of the treatment equipment insertion portion 31 via the packing 64 made of rubber in a watertight and airtight manner.

The tip side of the suction-side collet 36 is fixed to the exterior member 31a via the above resin member 52. The recessed portion provided on the outer circumferential face of the tip side portion of the suction-side collet 36 is provided with a watertight and airtight O ring 65. Note that with the outer circumferential face of the resin member 52, watertightness and airtightness are retained by the above O ring 54.

The outer circumferential face of the tip side of the suction-side collet 36 is provided with a male screw portion. The suction-side collet 36 is fixed to the exterior member 31a by screwing of the nut 66 by pressing the step portion of the resin member 52. The upper end face of the nut 66 is covered with a rubber cover 67.

The inner circumferential face at the tip side in the suction-side collet 36 is formed with an enlarged diameter portion wherein the diameter is enlarged in a step manner, and the enlarged diameter portion has a small-diameter cylindrical portion 68a of the base end of the filter case 68 in the filter unit 34 inserted and detachably mounted.

The outer circumferential face of the small-diameter cylindrical portion 68a is provided with a circumferential groove, and the circumferential groove stores a packing 69.

Next, description will be made regarding the configuration of the filter unit 34, and the configuration of the vicinity of the treatment equipment insertion portion 31 in the event of the filter unit 34 being mounted.

As illustrated in FIG. 5, the opening portion 35a of the treatment equipment-side collet 35 protruding from the rear end face of the treatment equipment insertion portion 31 is detachably mounted with the mounting portion of the base end of a substantially cylindrical-shaped forceps plug main body 71 making up the forceps plug portion 41 of the filter unit 34.

With the forceps portion main body 71, vicinity of the rear end thereof is provided with a small-diameter opening portion 71a which opens small, and rear end thereof has a forceps plug 72 detachably mounted.

With the forceps plug 72, a semispherical-shaped recessed portion is provided to form a suction duct opening 72a for inserting treatment equipment, a notch 72b is provided at the center of a thin-thickness portion covering the semispherical-shaped recessed portion, usually maintains a closed-off state, and has a function such as a check valve wherein the notch 72b is opened by treatment equipment being inserted from the outside so as to press. The notch 72b is arranged to make up an opening at the operating unit side of the insertion unit side suction duct.

Also, in the vicinity of at the center of the axial direction of the cylindrical-shaped forceps plug portion main body 71a through hole for passing through in the direction orthogonal to the axial direction is provided, a cylinder body portion 68b extending in the lateral direction of the filter case 68 is inserted from one of the lateral direction, and the cylinder body portion 68b portion is mounted within the through hole.

Note that a ring 74 connected to the forceps plug 72 is loosely fitted to the outer circumference of the cylinder body portion 68b, and even if the forceps plug 72 is removed from the forceps plug main body 71, the forceps plug 72 is arranged so as to be retained in the periphery of the cylinder body portion 68b.

Also, a cylinder body portion 75a at the base end side of a duct switchover knob 75 is rotatably mounted in the through hole from the other lateral direction in a state of being fitted into the above cylinder body portion 68b. Note that with the duct switchover knob 75, a rib 75f is formed at a position around an entrance to be fitted into the forceps plug portion main body 71. Thus, the duct switchover knob 75 is arranged so as to be sealed in a watertight and airtight manner at the time of the duct switchover knob 75 being fitted into the forceps plug portion main body.

With the duct switchover knob 75, a through hole is provided at a position of around the rear end of the cylinder body portion 75a in the direction orthogonal to axial direction thereof. In a mounting state illustrated in FIG. 5, this through hole has the function of the treatment equipment insertion duct 75b for connecting between the suction duct opening 72a and the treatment equipment-side collet opening portion 35a.

Note that in the event of rotating the duct switchover knob 75 90 degrees from the state in FIG. 5, the treatment equipment insertion duct 75b using the through hole of the duct switchover knob 75 is closed off by the inner wall face of the forceps plug portion main body 71. The treatment equipment-side collet opening portion 35a is in a state of closing off the suction duct opening 72a and a later-described filter-side duct 75e by the rotated duct switchover knob 75.

In a connecting state such as illustrated in FIG. 5, a surgeon inserts an unshown treatment equipment from the suction duct opening 72a, whereby the tip side of the treatment equipment can be inserted into the treatment equipment insertion tube 44 side via the treatment equipment insertion duct 75b, treatment equipment-side collet 35, and treatment equipment-side pipe 46 using this through hole.

Also, in this connecting state, the treatment equipment-side collet 35 is connected to the filter-side duct 75e formed by the inner side of the cylinder body portion 75a via the treatment equipment insertion duct 75b, and also is connected to the suction-side collet 36 side via the inside of the filter portion 42 connected to the filter-side duct 75e.

To the filter case 68 of the filter portion 42, a filter main body 77 to which a filter 77a is attached from rear end side opening thereof is detachably mounted so as to move rotationally. With the filter main body 77, the filter 77a is integrally provided by forming a small opening in a tetragonal lattice shape (mesh shape), transmitting liquid or gas, and performing retrieving of tissue such as a polyp piece having a certain size or larger.

The filter face of the filter 77a is disposed in parallel with the axial direction of the cylindrical filter case 68 so as to face the filter-side opening portion 75c of the end portion of the filter-side duct 75e.

Also, with the filter 77a, a substantially disc-shaped bottom face 77b is provided on bottom portion thereof, which forms a tissue-storing chamber (tissue-retrieving chamber) 68c for storing tissue retrieved within the filter case 68. Note that the filter face is provided at a position eccentric from the center axis of the cylindrical filter case 68, and the tissue-storing chamber 68c having large space is formed at a rotational moving position illustrated in FIG. 5.

That is to say, the connecting state illustrated in FIG. 5 illustrates a state in which the filter portion 42 in the filter unit 34 is set to a rotational moving position for performing retrieving of tissue.

In this state, the capacity of the tissue-storing chamber 68c facing the filter-side duct 75e is arranged so as to be increased.

Note that the filter case 68 of the filter portion 42 is made up of a transparent member so as to visually recognize the internal filter 77a and the retrieved (stored) tissue from the outside, and also the filter 77a is also colored with a blue system color for example which can be readily distinguished from an ordinary color of body tissue.

Also, in the event of cleansing the filter case 68 in cleaning liquid or the like, a part thereof is formed as a colored portion other than a solid color, or a colored member is provided so as to visually recognize that the filter case 68 is in cleaning liquid. This coloring may be, for example, that the packing 69 provided on the outer circumferential face of the small-diameter cylindrical portion 68a is colored in black or the like.

With the filter main body 77, a circumferential groove is provided on the outer circumferential face further toward the rear end side than a position where the filter 77a is provided, where an O ring 78 for seal is stored. Also, a filter-position switchover knob 77c provided at the rear end of the filter may body 77 protrudes from the opening end of the filter case 68, which facilitates a mounting/detaching operation, and a rotational moving operation.

Note that as illustrated in FIG. 5, in the connecting state, a slipping-prevention end portion 75d is formed for restricting the removal of the filter main body 77 from the filter case 68 such that a part (lower end in FIG. 5) of the circumferential edge portion of the filter-side opening portion 75c of the end portion of the filter-side duct 75e protrudes toward the inside of the filter case 68.

Upon the duct switchover knob 75 being rotated 90 degrees from this state, the slipping-prevention end portion 75d becomes a state of retreating into the cylinder body portion 68b from a state of protruding into the filter case 68, which enables the filter main body 77 to be removed from the filter case 68.

Also, with the present embodiment, an arrangement is made wherein a surgeon rotates the filter-position switchover knob 77c approximately 90 degrees or so from the filter position of the connecting state illustrated in FIG. 5, and sets to a position where tissue is not retrieved as illustrated in FIG. 4, whereby suction can be performed without passing through the filter 77a.

That is to say, as illustrated in FIG. 4, upon the surgeon setting to an OFF position where tissue is not retrieved by matching the position of a triangle mark 77f provided on the filter main body 77 to the position of a triangle mark 68d provided on the filter case 68, a (L-shaped) notch 77d illustrated on the substantially disc-shaped bottom face 77b in FIG. 7 is arranged so as to be formed at a position near the filter-side duct 75e.

Upon setting to a suction state, body fluid or the like sucked in via the notch 77d is arranged so as to be guided to the suction-side collet 36 side without passing through the filter 77a.

Note that with the filter main body 77, a label indicating ON for guide to set the filter 77a to a retrieving position and rotational direction thereof is provided as illustrated in FIGS. 6 and 7. Accordingly, arrangement is made wherein the surgeon moves rotationally the filter-position switchover knob 77c of the filter main body 77 in the direction along the label of ON up to the position where rotational movement is restricted, whereby the surgeon can set to the filter position where retrieving of tissue illustrated in FIG. 5 is performed.

Also, with the filter unit 34 in a disassembled state illustrated in FIG. 7, following the cylinder body portion 68b (into which the ring 74 of the forceps plug 72 is loosely fitted) in the filter case 68 being inserted from the right side of the forceps plug portion main body 71, and being mounted, the cylinder body portion 75a of the duct switchover knob 75 is inserted from the left side to be mounted on the inner side of the cylinder body portion 68b.

Also, the forceps plug 72 is mounted from the rear end of the forceps plug portion main body 71. Also, the filter main body 77 is mounted on the opening portion of the rear end of the filter case 68, which can be integrally assembled such as the filter unit 34 illustrated in FIG. 6.

The surgeon inserts the small-diameter cylindrical portion 68a of the base end of the filter portion 42 in the assembled filter unit 34 so as to fit into the opening portion 36a of the suction-side collet 36, and performs work for covering the opening portion 35a of the tip of the treatment equipment-side collet 35 with the base end of the forceps plug portion 41 by utilizing elasticity thereof, whereby the surgeon can detachably mount the filter unit 34 such as illustrated in FIG. 4.

With the present embodiment thus configured, the filter unit 34 for retrieving tissue is detachably provided on the way of the suction duct to be used for suction at closer to the tip side than the suction switchover valve 37 of the operating unit 8 of the endoscope 2, which is a feature of the present embodiment. Note that this suction duct is a collective term for the treatment equipment-side duct 30 and suction-side duct 32.

That is, the filter unit 34 for retrieving tissue is detachably disposed partway on the tip side of the suction duct, which is opposite side of one end to which the suction device 6 having the suction pump 6a built-in, namely the other end of the suction duct, with respect to a position of the suction switchover valve. Note that the filter unit 34 is disposed further toward the one end to which the suction device 6 is connected than the treatment equipment-side opening portion 35a which is the suction duct opening.

Also, with the present embodiment, in the event that the filter unit 34 for retrieving tissue is mounted, and a state is set wherein tissue can be sucked in by a suction operation, the slipping-prevention end portion 75d of the tip of the duct switchover knob 75 forms a removal restriction mechanism for restricting that the filter main body 77 is removed.

The duct switchover knob 75 is rotated 90 degrees from this state, thereby closing off the duct further toward the tip side than the tissue-storing chamber 68c, specifically, the opening portion 35a of the rear end of the treatment equipment-side collet 35, and also canceling the above removal restriction to form a mounting/detaching mechanism wherein the filter main body 77 can be removed, which is also a feature of the present embodiment.

That is to say, the duct switchover knob 75 is rotated 90 degrees from the state in which tissue can be retrieved by a suction operation, thereby closing off the duct further toward the tip side than the tissue-storing chamber 68c, specifically, the filter-side duct 75e. This closing-off enables the filter case 68 portion to be prevented from being opened externally (opened to the ambient atmosphere) at the time of removing the filter main body 77. Also, even during endoscopy, this closing-off makes it unnecessary to perform work for decreasing coelomic inner pressure by performing suction before the filter main body 77 is removed, whereby mounting/detaching of the filter main body 77 can be readily performed.

Also, with the present embodiment, closer to the suction connector 10a side than the suction duct portion where treatment equipment is inserted, i.e., on the way of the suction-side duct 32 further toward the rear end side than the treatment equipment-side duct 30 the filter unit 34 for retrieving tissue is provided, which is also a feature of the present embodiment.

In addition, with the present embodiment, of the suction duct to be segmentized by the filter unit 34 serving as a mounting/detaching duct member, the treatment equipment-side duct (insertion-unit-side suction duct) 30 serving as the insertion-unit tip side portion, and the suction-side duct (operating-unit-side suction duct) 32 serving as the side toward the surgeon are arranged at least in the vicinity of the treatment equipment insertion portion 31 to which the filter unit 34 is mounted such that the center distance between the axis of the treatment equipment-side duct 30 and the axis of the suction-side duct 32 is gradually extending toward the filter unit 34, which is also a feature of the present embodiment.

Specifically, as illustrated in FIG. 5, these have an angle of θ, and are arranged such that the center distance is extending as approaching the side toward the surgeon. Further, as illustrated in FIG. 4, the forceps plug portion 41 is provided at a position equivalent to the right side as viewed from the surgeon, and the tissue-retrieving portion is provided at a position equivalent to the left side, which is also a feature of the present embodiment. Thus, the surgeon can operate treatment equipment necessary for complex operations by the right hand without being hindered by the filter portion 42 side, thereby enabling surgeons of which right-handed persons are regarded as majority to operate treatment equipment with higher operability.

Also, as illustrated in FIG. 5, the upper end of the filter-position switchover knob 77c is higher at the side toward the surgeon than the upper end of the forceps plug 72 by a height H, which is also a feature of the present embodiment. Thus, ease of mounting/detaching of the filter main body 77 can be improved. At this time, the filter-position switchover knob 77c is formed in a general plate shape, so that the filter main body 77 can be mounted or detached without giving influence upon the forceps plug main body 71 by the surgeon's finger.

As illustrated in FIG. 5, the treatment equipment insertion duct 75b of the duct switchover knob 75 is arranged so as to become a straight line as to the duct within the treatment equipment-side collet 35 in a connecting state, and also arranged so as to become a straight line as to the notch 72b of the forceps plug 72, which is also a feature of the present embodiment. Thus, the surgeon can insert or remove treatment equipment along a straight line, and can prevent damage and the like of the treatment equipment.

In addition, the duct switchover knob 75 is disposed at the branch portion between the treatment equipment-side duct 30 and the suction-side duct 32, which is also a feature of the present embodiment. Thus, insertion and closing-off of the suction duct can be readily switched without complicating the configuration by a simple operation such as rotating the duct switchover knob 75.

At this time, more specifically, when removing the filter main body 77, the duct switchover knob 75 serving as a member for closing off the duct toward the suction-side collet 36 is arranged so as to be disposed in the cylinder body portion 68b serving as a connection duct for connecting the forceps plug 41 and the filter portion 42. Thus, it becomes unnecessary to separately provide a member for securing closing-off at the time of removing the filter main body 77, which enables the filter portion 42 for retrieving tissue to be reduced in size.

Further, the diameter K of the treatment equipment insertion duct 75b of the duct switchover knob 75 illustrated in FIGS. 5 and 7 is arranged so as to be greater than the minimum value of the diameter of the treatment equipment-side duct 30. As for one example, the diameter K of the treatment equipment insertion duct 75b is greater than the diameter M of the duct portion of the treatment equipment-side pipe 46 illustrated in FIG. 5. Thus, even if the duct switchover knob 75 is provided, the same ease of insertion/removal of treatment equipment as the conventional endoscope in which the duct switchover knob 75 is not provided can be secured.

Description will be made regarding operations of the present embodiment thus configured.

As illustrated in FIG. 1, a surgeon mounts the filter unit 34 on the treatment equipment insertion portion 31 of the endoscope 2, and inserts this endoscope 2 into the body cavity of a patient.

Subsequently, the surgeon enters a portion to be checked such as an affected portion or the like into an observation field of view using the image capturing means provided in the tip portion 11 of the insertion unit 7, and sets the captured image to an observable state using the color monitor 5.

Subsequently, in the event of desiring to retrieve tissue such as a polyp of an affected portion to perform biopsy, the surgeon inserts the tip side of an excision treatment equipment from the suction duct opening 72a in the filter unit 34, and then excises the tissue such as a polyp or the like.

In the event of having retrieved the excised tissue to terminate the endoscopy, while keeping a state in which the surgeon is gripping the tissue by the treatment equipment protruding from the tip of the endoscope 2, the surgeon should remove the endoscope 2 from the inside of the body. However, in the event of continuing the endoscopy even after retrieving the excised tissue, the surgeon removes the treatment equipment from the treatment equipment-side duct 30.

In the event of setting a suction state by operating the suction switchover valve 37, the surgeon sets the filter 77a of the filter main body 77 to a position where retrieving of tissue is performed as illustrated in FIG. 5 beforehand.

Thus, the surgeon can suck the excised tissue into the treatment equipment-side duct 30 from the tip opening in the treatment equipment-side duct 30 provided in the longitudinal direction of the insertion unit 7.

The surgeon can store the sucked-in tissue in the tissue-storing chamber 68c of the filter portion 42. In this case, the surgeon can guide body fluid or the like to the suction pump 6a side through a small hole of the filter 77a, and store this in an unshown suction-trap container or the like.

In the event of completing retrieving (storing) of the tissue into the tissue-storing chamber 68c by operating the suction switchover valve 37, the surgeon rotationally moves the duct switchover knob 90 degrees from the state illustrated in FIG. 5 to set the opening portion 35a of the treatment equipment-side collet 35 to a closed-off state, following which performs an operation for separating the filter main body 77 from the filter case 68. Thus, the surgeon can remove the filter main body 77 from the filter unit 34. Subsequently, the surgeon can employ the tissue, which is adhered to the filter 77a of the filter main body 77 and thus retrieved, in biopsy.

In this case, according to the present embodiment, the filter 77a is provided in the vicinity of the treatment equipment insertion portion 31 for inserting treatment equipment, i.e., at a position further toward the tip side than the suction switchover valve 37, so that the duct length in the event of passing tissue through the treatment equipment-side duct 30 by suction can be shortened, the possibility that the tissue may be subjected to deformation and the like at the time of passing through the duct can be reduced, and also necessary tissue can be retrieved in a short period of time.

Also, the filter 77a is disposed at further toward the tip side than the suction switchover valve 37, so that receiving influence of a narrowed portion and a bending portion in the vicinity of the suction switchover valve 37 can be eliminated. That is to say, deterioration in permeability of the tissue in the vicinity of the suction switchover valve 37 and thus taking time to retrieve the tissue can be eliminated, and also the possibility of deforming and damaging the tissue can be eliminated.

Also, with the present embodiment, the filter 77a portion is provided detachable from the filter main body 77 as to the endoscope 2, and accordingly, the surgeon can easily and smoothly perform work from retrieving tissue to biopsy thereof.

Also, according to the present embodiment, the filter main body 77 having the filter 77a in the suction-side collet 36 adjacent to the base end side of the treatment equipment-side collet 35 for inserting treatment equipment is arranged so as to be detachable, so that the surgeon can insert treatment equipment to perform treatment using the treatment equipment even in a state of mounting the filter main body 77.

On the other hand, in the event of performing endoscopy or the like using the endoscope 2 without retrieving of tissue, the surgeon should set the position of the triangle mark 77f provided on the filter-position switchover knob 77c of the filter main body 77 to an OFF position where tissue is not retrieved. Thus, the surgeon can discharge an aspirate sucked in such as body fluid or the like to the suction pump 6a side via the suction-side duct 32 and suction connector 10a without passing through the filter 77a.

Note that the above filter unit 34 can be regarded as a tissue-retrieving filter including a forceps-plug function, and also can be regarded as a forceps plug including a tissue-retrieving-filter function.

With the filter unit 34, a part of the suction duct in the endoscope is arranged so as to be detachable (detachable duct member), which is a member including branch of the suction duct (i.e., the insertion-unit-side suction duct and operating-unit-side suction duct) to be segmentized by the filter unit 34 itself. Accordingly, the filter unit 34 is detachable, so that we can say that the detachable duct member, filter portion, and forceps plug are integrally detachable.

According to such a first embodiment, the branch between the insertion-unit-side suction duct and the operating-unit-side suction duct is provided at the forceps plug side, and accordingly, the branch of the suction duct is not provided at the endoscope main body side, whereby the cleaning properties of the endoscope main body can be improved.

The filter unit 34 including a function as a forceps plug can be separated into the forceps plug portion main body 71, forceps plug 72, duct switchover knob 75, filter case 68, and filter main body 77 as illustrated in FIG. 7, and thus, a brush can be inserted into a duct connected to the opening portion of each part in parallel to the axis of the duct, thereby improving cleaning properties.

Also, a function as a forceps plug and a function as a tissue-retrieving filter are integrated as a filter unit, and thus, the filter unit can be integrally mounted or detached from the endoscope main body, whereby effort for mounting or detaching at the time of cleaning can be reduced.

The filter portion 42 is disposed in the vicinity of the treatment equipment insertion portion 31 which is further toward the tip side than the suction switchover valve 37, and thus, the tissue sucked in being influenced by the narrowed portion, and the bending portion in the vicinity of the suction switchover valve 37, can be eliminated. That is to say, deteriorating permeability of tissue in the vicinity of the suction switchover valve 37 and thus taking time to retrieve the tissue can be eliminated, and also deforming and damaging of the tissue can be eliminated.

Also, when the duct switchover knob 75 is in a suction state, the filter main body 77 is hindered from insertion or removal, and accordingly, leakage of body fluid or the like caused by the filter main body 77 being removed carelessly can be prevented. Only when the duct switchover knob 75 is in a closed-off state, the filter main body 77 can be removed, so even if the filter main body 77 is removed, the pressure within the body cavity can be prevented from deterioration.

Further, the filter case 68 is formed of a material having optical transparency, which allows a surgeon himself/herself to readily confirm at the side toward the operating unit whether or not tissue has been retrieved. At this time, the filter unit 34 is mounted on the treatment equipment insertion portion 31, which allows the surgeon or an assistant to readily visually recognize the filter unit 34, as illustrated in FIG. 8. Thus, retrieving of tissue at this position can be readily performed as compared with a case of retrieving of tissue on the way of the universal cable 9, or in the vicinity of the suction device 6.

In addition, the suction-side duct 32 serving as an operating-unit-side suction duct is not provided in the outside of the operating unit 8 but in the inside thereof, which does not hinder the surgeon gripping the operating unit 8.

(Second Embodiment)

Next, description will be made regarding a second embodiment of the present invention.

Figure 9:
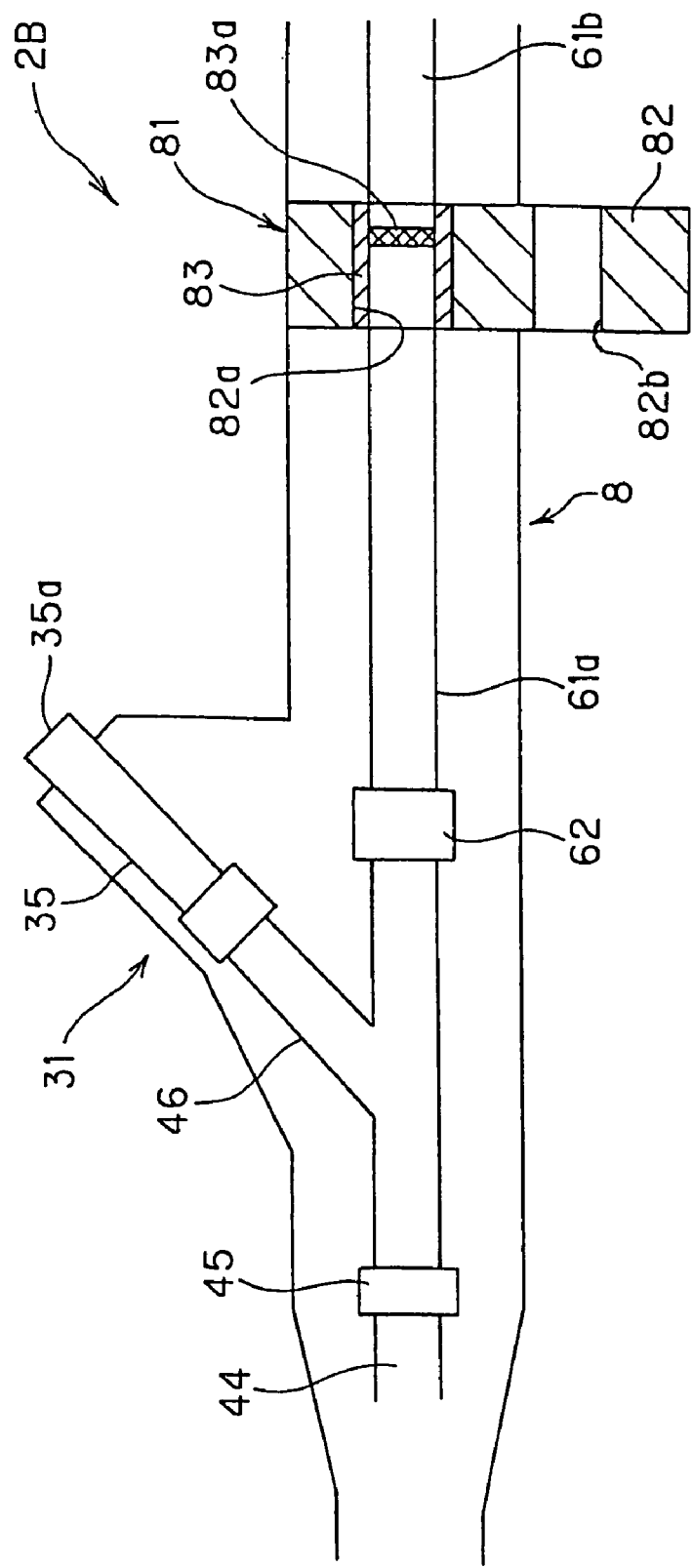
FIG. 9 is a diagram illustrating the outline configuration of the periphery of an operating unit with an endoscope according to a second embodiment of the present invention.

FIG. 9 illustrates the schematic configuration of the periphery of the operating unit in an endoscope 2B according to the second embodiment of the present invention. The endoscope 2B according to the present embodiment has an arrangement wherein with the endoscope 2 according to the first embodiment, a branch portion is provided in the treatment equipment-side pipe 46, one is connected to the treatment equipment-side collet 35, and the other is connected to the suction-side pipe 61 in a substantially direct pipe shape.

Also, the tissue-retrieving filter case 81 is arranged so as to be detachably mounted on the way of the suction-side pipe 61 further toward the tip side than the suction switchover valve 37 from the side portion of the operating unit 8.

To the operating unit 8, for example, a rectangular-shaped through hole crossing the suction-side pipe 61 is provided in the direction orthogonal to the axis of the operating unit 8. This through hole stores a rectangular-shaped filter case 81 which is slidable in the depth direction. Note that the suction-side pipe 61 further toward the tip side than this through hole is represented with 61a, and the suction-side pipe 61 further backward than the through hole is represented with 61b.

To the filter case 81, two through holes 82a and 82b are provided at an interval which is greater than the inside diameter of the suction-side pipe 61 so as to be orthogonal (transverse) to the longitudinal direction of the rectangular shape. The first through hole 82a stores a cylindrical filter member 83 to which a mesh-shaped filter 83a is detachably attached. Also, the second through hole 82b is arranged to be generally the same as the inside diameter of the suction-side pipe 61. Note that the rectangular-shaped filter case 81 is made up of a member made of rubber including airtight and watertight functions.

As illustrated in FIG. 9, an arrangement is made wherein the surgeon sets the first through hole 82a to a state of connecting the suction-side pipes 61a and 61b, and sets a suction state by operating the suction switchover valve 37, whereby the filter 83a hinders tissue from passing through to enable the tissue to be stored.

Also, an arrangement is made wherein the surgeon presses the lower end side of the filter case 81 from the state in FIG. 9 to move the filter case 81 to the upward side within the through hole, and sets the second through hole 82b to a state of connecting the suction-side pipes 61a and 61b, whereby the surgeon can remove the filter member 83 to which the filter 83a is attached from the filter case 81.

Description will be made regarding operations according to the present embodiment thus configured.

In the event of retrieving tissue, the surgeon sets to the state illustrated in FIG. 9, and operates the suction switchover valve 37 to set to a suction operating state. Thus, the tissue sucked in is hindered by meshes of the filter 83a from passing through to be stored in the vicinity of the filter 83a.

In the event of completing retrieving of a predetermined amount of tissue, the surgeon presses the lower end of the filter case 81 to move the filter case 81 to a position in the outside of the operating unit 8 where the filter member 83 can be removed. Thus, the surgeon can remove the filter member 83 from the filter case 81. Also, in this state, the second through hole 82b connects the suction-side pipes 61 a and 61b, so the surgeon can perform an ordinary suction operation without trouble.

Figure 10:
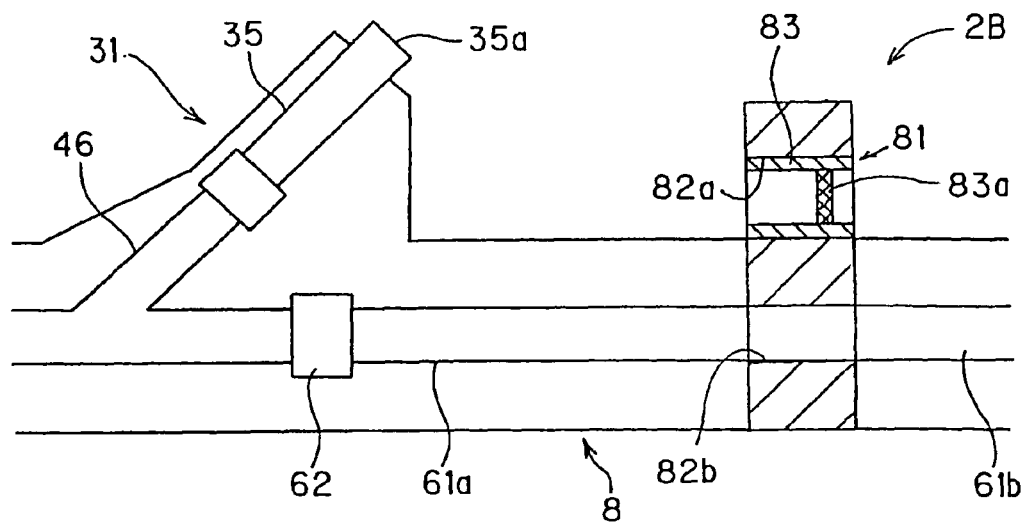
FIG. 10 is a diagram illustrating a state in which a filter case is moved up to a position where a filter member can be removed in FIG. 9.

Also, an arrangement is made wherein while the surgeon is moving the filter case 81 from the state in FIG. 9 to the state in FIG. 10, at least the opening end of the suction-side pipe 61 a of the tip side is not opened externally (opened to the ambient atmosphere) at a portion between the first through hole 82a and the second through hole 82b in the filter case 81.

According to the present embodiment, even in a state in which the tissue-retrieving filter case 81 is mounted, which is mounted at a position different from a position serving as the treatment insertion entrance where a treatment equipment is inserted, insertion using treatment equipment can be performed in the same way as an existing endoscope.

Also, according to the present embodiment, retrieving of tissue can be easily performed. Also, even with the present embodiment, tissue can be retrieved without being affected by the periphery of the suction switchover valve 37.

Further, according to the present embodiment, the present embodiment can be realized even with an existing endoscope, by modifying the configuration within the operating unit 8.

Figure 11:
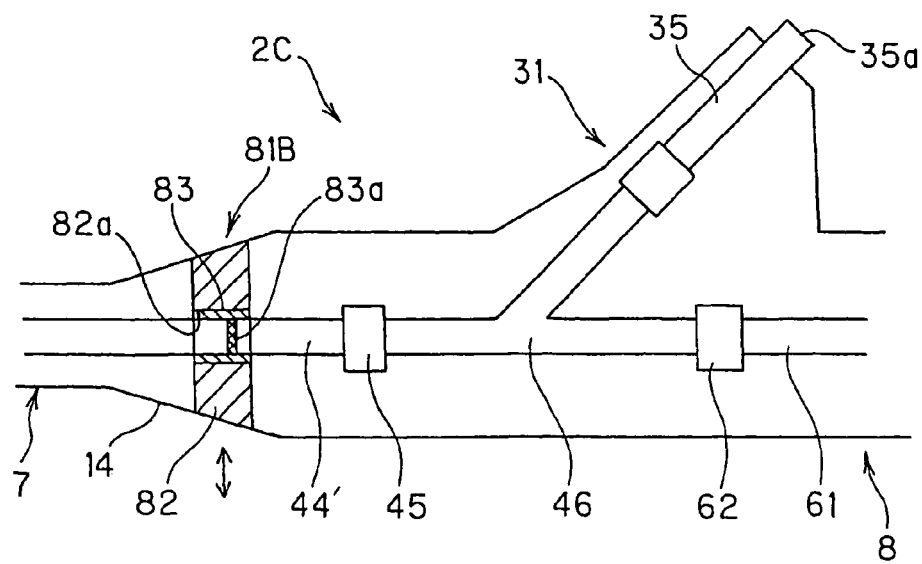
FIG. 11 is a diagram illustrating the outline configuration of the periphery of a folding-prevention unit with a modification.

Next, description will be made regarding modifications with reference to FIG. 11. FIG. 11 illustrates a part of an endoscope 2C according to a modification. In the endoscope 2C, a filter case 81 B is detachably provided in the vicinity of the folding-prevention portion 14 which is thickened in a tapered shape in the vicinity of the rear end of the insertion unit 7, for example. That is, the filter case 81 B is detachably provided in the vicinity of the base end of the endoscope insertion unit 7.

That is to say, with the folding-prevention portion 14, a though hole is provided so as to cross treatment equipment insertion tube 44' in the direction orthogonal to longitudinal direction thereof, and the filter case 81 B is mounted slidably.

The filter case 81 B has the same configuration as the configuration of the filter case 81 according to the second embodiment wherein the second through hole 82b is not provided.

In the event of retrieving tissue, the surgeon should set to the state illustrated in FIG. 11 as with FIG. 9. Also, in the event of removing the filter member 83 from the filter case 81 B, as illustrated with the arrow, upon moving the filter case 81 B to the upward side, the filter member 83 to which the filter 83a is attached can be removed.

In the event of not retrieving tissue, upon the filter case 81 B from which the filter member 83 is removed being set to the state illustrated in FIG. 11, this can be used by inserting treatment equipment, or the like. Also, suction and discharge and so forth of fluid can be performed by suction.

As for the other modification, a filter member in which a filter is attached to the tip portion 11 of the insertion unit 7 may be provided, for example.

With the above-described invention, the tissue-retrieving filter portion for retrieving tissue by suction is provided on the way of the suction duct at further toward the tip side than the suction switchover valve, so in the event of performing biopsy by retrieving tissue from a portion such as a polyp or the like at the time of endoscopy, retrieving of tissue or the like can be smoothly performed.

(Third Embodiment)

Next, description will be made regarding a third embodiment with reference to FIGS. 12 through 16.

Figure 12:
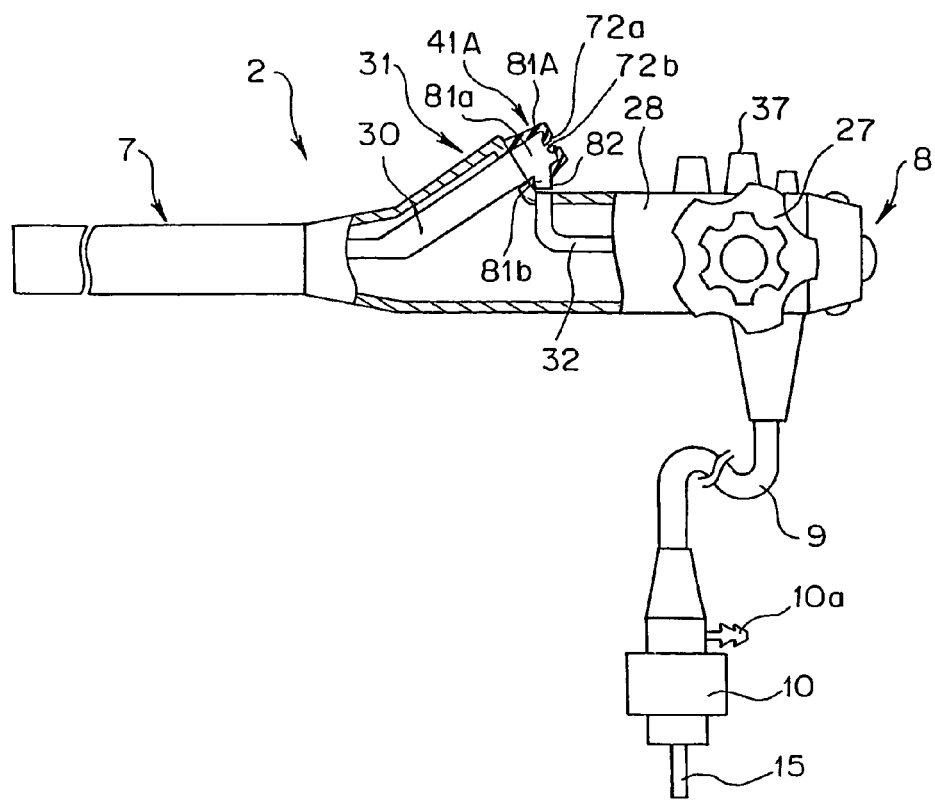
FIG. 12 illustrates a first configuration example of a forceps plug with an endoscope according to a third embodiment of the present invention, which is a side view including a part of cross-section of the endoscope.

FIG. 12 is a side view including partially the cross-section of an endoscope, which illustrates a first configuration example of a forceps plug.

As described above, the treatment equipment-side duct 30 also serves as treatment equipment insertion path for inserting treatment equipment such as forceps or the like, one end is opened at the tip of the insertion unit 7, and the other end is opened at the operating unit (handy operating unit) 8 without branching on the way thereof. Specifically, the treatment equipment-side duct 30 is opened at the opening portion 35a of the treatment equipment-side collet 35.

The suction-side duct 32, which is disposed passing through the inside of the operating unit 8, is configured such that one end within the operating unit 8 of the suction-side duct 32 is opened in the vicinity of the opening at the operating unit side of the treatment equipment-side duct 30, and the other end side is connected to the suction switchover valve 37. Specifically, the suction-side duct 32 is opened at the opening portion 36a of the suction-side collet 36.

The suction-side duct 32 is bent, for example, in an L-shape so as to cross (e.g., generally orthogonal) as to the axis of the operating unit 8 in the vicinity of the opening at the operating unit side. Accordingly, with this modification, the opening at the operating unit side of the suction-side duct 32 is positioned at the side face of the tip side of the gripper 28.

A forceps plug portion 41A is detachably mounted on the opening at the operating unit side of the treatment equipment-side duct 30. The forceps plug portion 41A includes a main body 81A made up of an elastic body, and the inside of the main body 81A is provided with a duct 81 a configured so as to connect to the treatment equipment-side duct 30, and a connection duct 81b configured so as to branch from the duct 81a and connect to the suction-side duct 32.

The rear end of the duct 81a is provided with the suction duct opening 72a including the notch 72b. As described above, the suction duct opening 72a is configured so as to achieve a function as a back-flow prevention valve for preventing the air within a body cavity from leaking externally (or deflating) when the air pressure within the body cavity is higher than the external air pressure by the surgeon expanding the body cavity with air supply so as to readily observe the inside of the body cavity. Also, a part of the connection duct 81b is provided within the main body 81A, and another part thereof is provided within the duct portion 82 extending from the main body 81A.

The forceps plug portion 41A thus configured can perform connection to the opening at the operating unit side of the suction-side duct 32 (the opening portion 36a of the suction-side collet 36), and connection to the opening at the operating unit side of the treatment equipment-side duct 30 (the opening portion 35a of the treatment equipment-side collet 35) simultaneously, simply by being attached to the treatment equipment insertion portion 31.

According to a configuration such as illustrated in this example, it is unnecessary to bend the suction-side duct 32 in a U- shape, and the curvature R of a bending portion can be made relatively great, which provides an advantage wherein ease of insertion of a brush when cleaning the inside of the duct is excellent.

Figure 13:
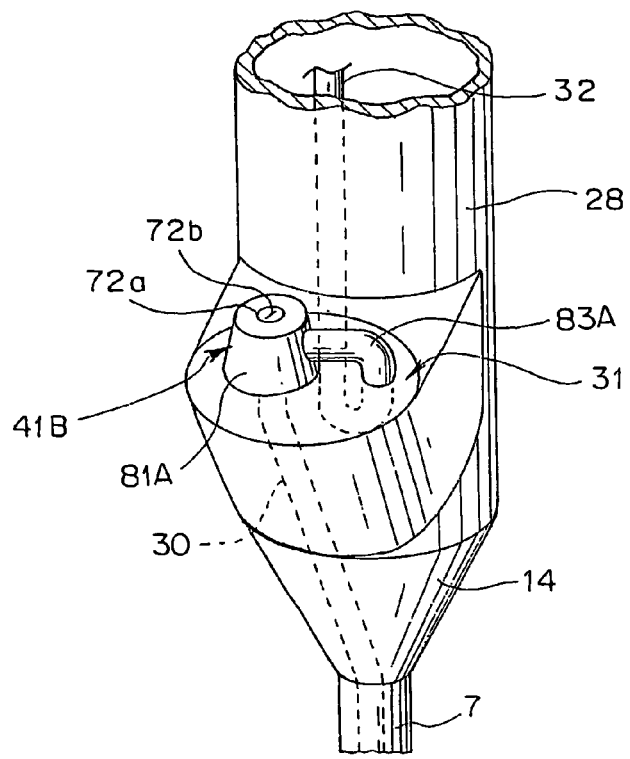
FIG. 13 illustrates a second configuration example of a forceps plug with an endoscope according to the third embodiment of the present invention, which is a partial enlarged perspective view of the vicinity of the treatment equipment insertion portion of the endoscope.

FIG. 13 is a partial enlarged perspective view in the vicinity of the treatment equipment insertion portion of the endoscope, which illustrates a second configuration example of a forceps plug.

With the second configuration example, the suction-side duct 32 is bent in the vicinity of the opening at the operating unit side (the opening portion 36a of the suction-side collet 36) so as to return to a U-shape at the side toward the hand side, as with the configuration example illustrated in FIG. 3. The opening at the operating unit side of the suction-side duct 32 and the opening at the operating unit side of the treatment equipment-side duct 30 are arrayed and disposed so as to have generally the same distance as to the axis of the operating unit 8.

Accordingly, the opening at the operating unit side of the treatment equipment-side duct 30 (the opening portion 35a of the treatment equipment-side collet 35) and the opening at the operating unit side of the suction-side duct 32 (the opening portion 36a of the suction-side collet 36) have the positional relation of being arrayed generally on the circumference centered on the axis of the operating unit 8, as with the example in FIG. 3.

The forceps plug portion 41B is configured wherein the main body 81A is attached to the opening at the operating unit side of the treatment equipment-side duct 30 (the opening portion 35a of the treatment equipment-side collet 35), and also a substantially L-shaped connection duct 83A to be connected to the opening at the operating unit side of the suction-side duct 32 (the opening portion 36a of the suction-side collet 36) is extended from the side face of the main body 81A. Also, the upper end portion of the main body 81A is provided with the suction duct opening 72a including the notch 72b as described above, which is connected to the treatment equipment-side duct 30.

According to such a configuration, the connection duct 83A to the suction-side duct 32 of the forceps plug portion 41B is positioned apart from the gripper 28, so that the surgeon is not hindered by the connection duct 83A at the time of gripping the gripper 28. Accordingly, even a surgeon having large hands can grip the endoscope 2 with room to spare.

Figure 14:
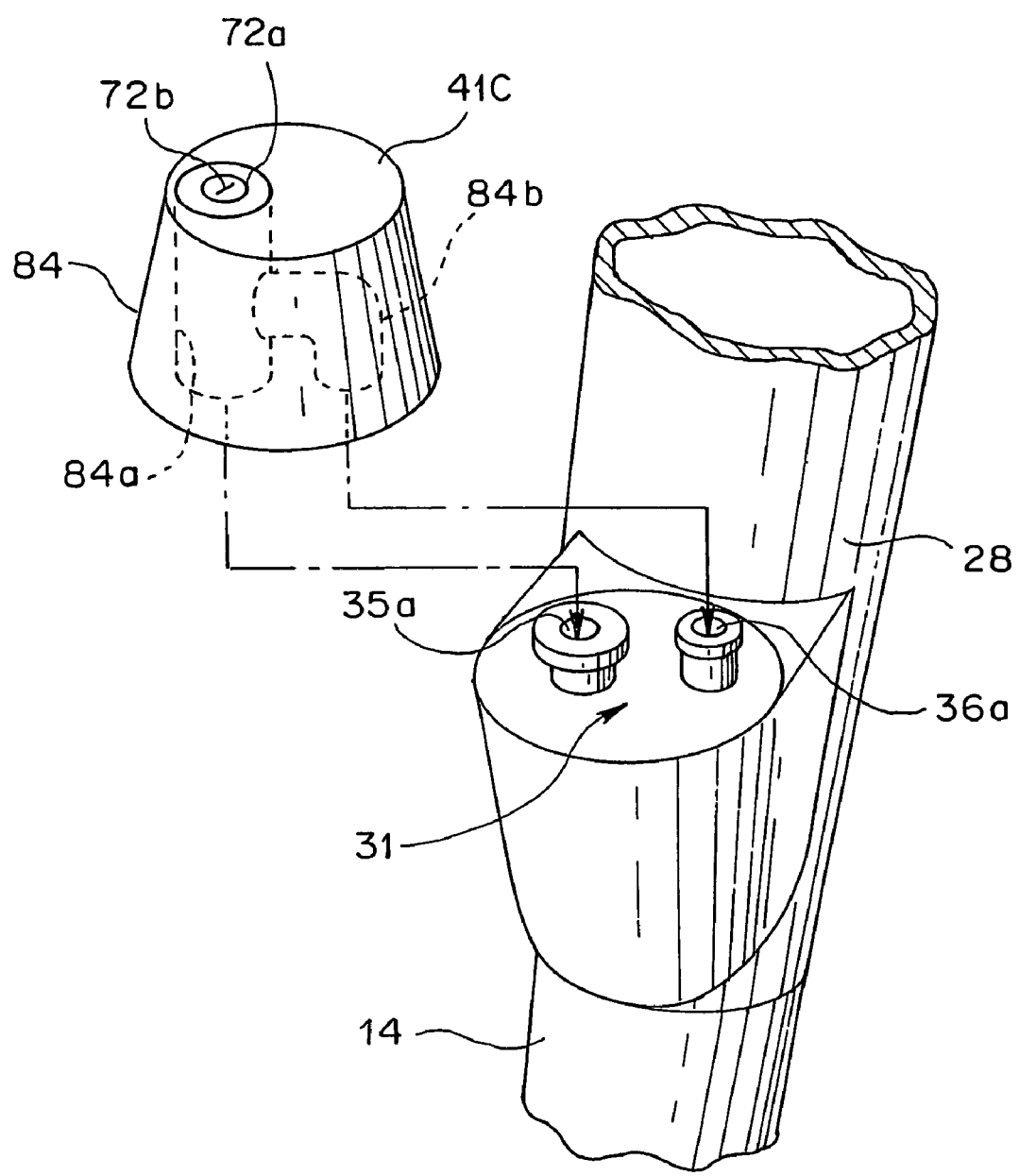
FIG. 14 is a perspective view illustrating the forceps plug of a third configuration example with the endoscope according to the third embodiment of the present invention, and the vicinity of the treatment equipment insertion portion to which the forceps plug is attached.

FIG. 14 is a perspective view illustrating the forceps plug according to the third configuration example, and the vicinity of the treatment equipment insertion portion of the endoscope to which this forceps plug is attached.

The forceps plug portion 41C illustrated in this third configuration example is integrally configured of the duct 84a to be connected to the opening portion 35a of the treatment equipment-side collet 35 connected to the treatment equipment-side duct 30, and the duct 84b, which is branched on the way of the duct 84a, to be connected to the opening portion 36a of the suction-side collet 36 connected to the suction-side duct 32, within the main body 84. Also, the rear end (upper end illustrated in FIG. 14) of the duct 84a is provided with the suction duct opening 72a including the notch 72b.

According to such a configuration, two or more ducts to be branched are provided within one member, which provides an advantage wherein the number of parts can be reduced.

Figure 15:
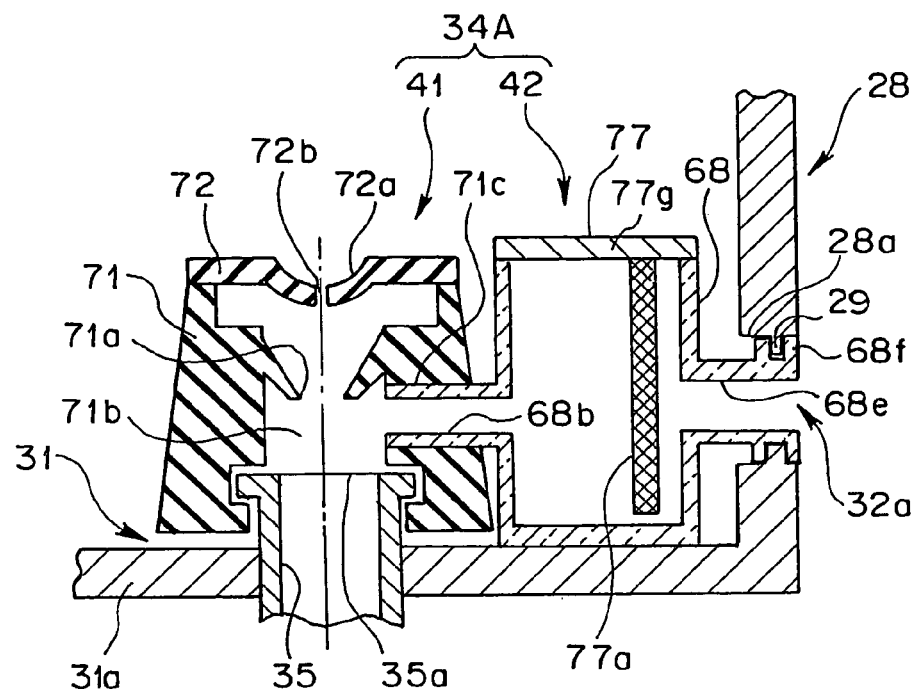
FIG. 15 is a cross-sectional view illustrating a first configuration example of a filter unit serving as a forceps plug including a filter portion with the endoscope according to the third embodiment of the present invention.

FIG. 15 is a cross-sectional view illustrating a first configuration example of a filter unit serving as a forceps plug including a filter portion.

This filter unit 34A comprises a forceps plug portion 41 made up of an elastic body such as rubber or the like, a forceps portion main body 71, and a forceps plug 72, such as described above.

The forceps plug portion 41 is arranged so as to be coupled in a watertight and airtight manner by being press-fit into the opening portion 35 of the treatment equipment-side collet 35 connected to the treatment equipment-side duct 30.

A side hole 71c is formed in the forceps plug portion 41 so as to become orthogonal to the treatment equipment insertion duct 71b within the forceps plug portion 41, and the cylinder body portion 68b of the filter case 68 is inserted into this side hole 71 c.

The filter portion 42 is configured by mounting the filter main body 77 within the filter case 68 so as to be detachable. The filter case 68 of these is formed in a substantially cylinder shape with a bottom of, for example, a transparent resin or the like having translucency, the cylinder body portion 68b for connecting to the forceps plug portion 41 such as described above are extending from the side face, and also the duct portion 68e for connecting to the exterior side of the gripper 28 is extended from the other side face.

An attachment portion 68f is formed on the tip of the latter duct portion 68e, and the attachment portion 68f is arranged so as to be attached by being fitted into the opening portion 28a of the exterior of the gripper 28. At this time, the recessed portion provided on the outer circumferential portion of the attachment portion 68f is attached with the O ring 29, and thus, the filter portion 42 is coupled with the gripper 28 in a watertight and airtight manner. Thus, the filter portion 42 is connected to the opening 32a at the operating unit side of the suction-side duct 32.

Note that the suction-side duct 32 of the endoscope 2 illustrated in this example is a type such as illustrated in FIG. 9, i.e., a type wherein the opening 32a at the operating unit side is provided on the side face of the gripper 28.

The filter main body 77 comprises a substantially disc-shaped lid portion 77g for closing the top face of the filter case 68 with a lid in a watertight and airtight manner, and a filter 77a formed so as to protrude into the filter case 68 from this lid portion 77g.

Thus, the filter 77a serving as a tissue-retrieving filter member is provided on the way of the connection duct made up of the cylinder body portion 68b and duct portion 68e, thereby enabling the filter unit 34A serving as a forceps plug to be employed for both the insertion of treatment equipment, and retrieving of tissue such as a polyp which is sucked in from a subject. Moreover, the filter case 68 is arranged so as to include translucency, so that regarding whether or not tissue has been retrieved can be readily confirmed. Accordingly, time required for diagnosis can be also reduced.

Figure 16:
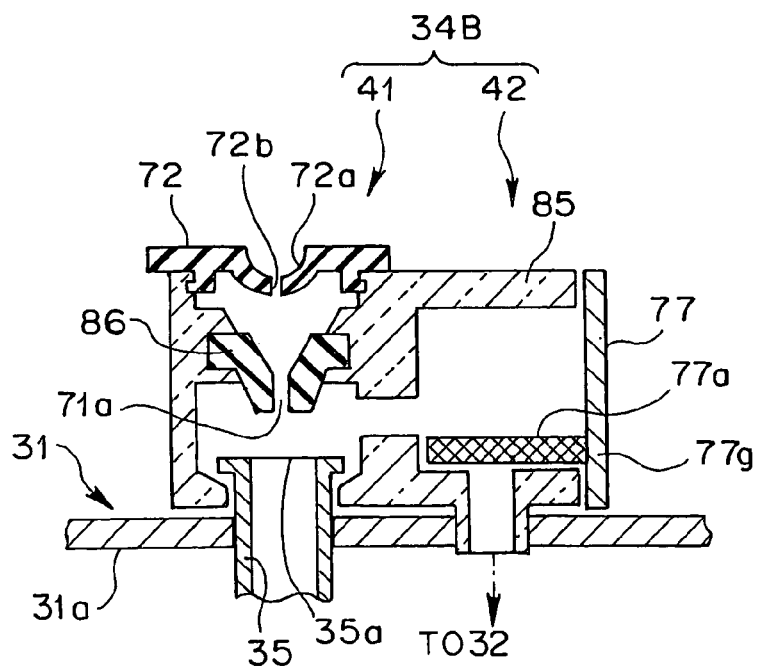
FIG. 16 is a cross-sectional view illustrating a second configuration example of a filter unit serving as a forceps plug including a filter portion with the endoscope according to the third embodiment of the present invention.

FIG. 16 is a cross-sectional view illustrating a second configuration example of a filter unit serving as a forceps plug including a filter portion.

A filter unit 34B comprises a main body 85 wherein the main body of the forceps plug portion 41 and the filter case of the filter portion 42 are integrally formed. The main body 85 is formed of, for example, a transparent resin or the like including translucency.

To the forceps plug portion 41 side of the main body 85, a forceps plug 72 made up of an elastic member such as rubber or the like, and an internal valve 86 made up of an elastic member such as rubber or the like so as to have a small-diameter opening portion 71 a are integrally attached.

Also, the filter portion 42 side of the main body 85 is arranged so as to be detachably attached with the filter main body 77 from the lateral side for example. Accordingly, the configuration of the filter main body 77 is basically the same as that illustrated in FIG. 16.

Employing such a configuration wherein the main body of the forceps plug portion and the filter case of the filter portion are integrally formed enables production cost to be kept low. Also, the filter case is transparent, so that regarding whether or not tissue has been retrieved can be readily confirmed.

Note that as shown in the above respective embodiments, as for the forceps plug portion, at least a part thereof is made up of an elastic body.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An endoscope comprising:
    an endoscope insertion unit including an observation window at a tip portion;
    a suction duct having a suction source end connected to a suction source, and a suction end located on the tip portion of the endoscope insertion unit;
    a suction switchover unit provided at a halfway part of the suction duct, the suction switchover unit switching over between suction ON/OFF states by the suction source; and
    a tissue retrieving unit for retrieving a living tissue sucked through the suction duct, the tissue retrieving unit being located on the suction duct between the suction end and the part of the suction duct where the suction switchover unit is provided, wherein
    the suction duct includes:
        a first duct having one end configuring the suction end and another end configuring a suction duct opening, the first duct serving also as a duct for a treatment equipment; and
        a second duct having one end configuring the suction source end and another end configuring an opening portion, and
    the tissue retrieving unit includes:
        a treatment equipment plug located on a suction duct opening side and capable of closing off the suction duct opening;
        a filter portion for retrieving a living tissue sucked through the first duct, the filter portion being coupled to the opening portion of the second duct;
        a connection duct for connecting the first duct and the filter portion;
        a filter provided to the filter portion and having a mesh-shaped opening for retrieving the living tissue;
        a tissue retrieving portion for retrieving the living tissue by hindering passage of the sucked living tissue by the filter;
        a filter main body including the filter, the filter main body being rotatably mounted to the opening portion of the second duct; and
        a switchover portion for switching over between a first state in which the living tissue passed through the connection duct is stored in the tissue retrieving portion by hindering the passage of the living tissue by the filter and a second state in which the connection duct is connected to the second duct so as to bypass the living tissue passed through the connection duct to a side of the second duct without the filter intervening between the connection duct and the second duct, depending on a rotational moving position of the filter main body.

2. The endoscope according to claim 1, wherein the connection duct includes a treatment equipment connecting portion for connecting the suction duct opening and the suction end.

3. The endoscope according to claim 2, wherein the connection duct includes:
    a first connection hindering portion for hindering connection between the first duct and the filter portion, and a second connection hindering portion for hindering connection between the suction duct opening and the suction end.

4. The endoscope according to claim 3, wherein the connection duct has a mechanism for simultaneously hindering the connection between the first duct and the filter portion and the connection between the suction duct opening and the suction end.

5. The endoscope according to claim 1, wherein the connection duct has a mechanism for preventing the filter portion from being separated from the second duct.

6. The endoscope according to claim 1, wherein the filter portion includes:
    a connection portion for connecting the connection duct and the second duct without the filter intervening therebetween in the second state.

7. The endoscope according to claim 1, wherein the filter main body is detachably mounted to the opening portion of the second duct.

8. The endoscope according to claim 7, further comprising a switchover knob provided so as to be rotatable around an axial direction of the connection duct wherein,
    the switchover knob includes a first hole at an axis portion so as to be located at a position facing the first duct in an axis direction of the switchover knob, the first through hole passing through in a direction substantially orthogonal to the axial direction of the switchover knob, and a second hole formed at the axis portion arranged in the axial direction of the connection duct, the second hole including one end connected to the first hole and another end which is open, and the switchover knob opens and closes the first duct according to a direction of the first hole which corresponds to a rotational moving position of the switchover knob, and opens and closes the connection duct in conjunction with the opening and closing of the first duct,
    wherein, in a rotational moving position at which the first duct is in an open state, the switchover knob further hinders removal of the filter main body from the opening portion of the second duct by an end portion protruding from the connection duct at the axis portion to the filter portion.

9. The endoscope according to claim 1, further comprising a switchover knob provided so as to be rotatable around an axial direction of the connection duct, wherein the switchover knob includes a first hole at an axis portion so as to be located at a position facing the first duct in an axis direction of the switchover knob, the first through hole passing through in a direction substantially orthogonal to the axial direction of the switchover knob, and a second hole formed at the axis portion arranged in the axial direction of the connection duct, the second hole including one end connected to the first hole and another end which is open, and the switchover knob opens and closes the first duct according to a direction of the first hole which corresponds to a rotational moving position of the switchover knob, and opens and closes the connection duct in conjunction with the opening and closing of the first duct.

10. An endoscope comprising:
    an endoscope insertion unit including an observation window at a tip portion;
    a suction duct having a suction source end connected to a suction source, and a suction end located on the tip portion of the endoscope insertion unit;
    a suction switchover unit provided at a halfway part of the suction duct, the suction switchover unit switching over between suction ON/OFF states by the suction source; and
    a tissue retrieving unit for retrieving a living tissue sucked through the suction duct, the tissue retrieving unit being located on the suction duct between the suction end and the part of the suction duct where the suction switchover unit is provided, wherein
    the suction duct includes:
        a first duct having one end configuring the suction end and another end configuring a suction duct opening, the first duct serving also as a duct for a treatment equipment; and
        a second duct having one end configuring the suction source end and another end configuring an opening portion, and
    the tissue retrieving unit includes:
        a treatment equipment plug located on a suction duct opening side and capable of closing off the suction duct opening;
        a filter portion for retrieving a living tissue sucked through the first duct, the filter portion being coupled to the opening portion of the second duct; and
    a connection duct for connecting the first duct and the filter portion, wherein the filter portion includes:
        a tissue retrieving portion for, by facing the connection duct, retrieving the sucked living tissue,
        a connection portion connected to the second duct, and
        a filter for partitioning between the tissue retrieving unit and the connection portion, and
    has a function for, by making the connection portion face the connection duct, connecting the connection duct and the second duct without the tissue retrieving portion intervening therebetween.

\* \* \* \* \*